(12) United States Patent
Irion

(10) Patent No.: US 8,048,675 B1
(45) Date of Patent: Nov. 1, 2011

(54) INTEGRATION-FREE HUMAN INDUCED PLURIPOTENT STEM CELLS FROM BLOOD

(75) Inventor: Stefan Irion, San Francisco, CA (US)

(73) Assignee: iPierian, Inc., South San Francisco, CA (US)

( * ) Notice: Subject to any disclaimer, the term of this patent is extended or adjusted under 35 U.S.C. 154(b) by 0 days.

(21) Appl. No.: 12/778,938

(22) Filed: May 12, 2010

(51) Int. Cl.
  *C12N 15/85* (2006.01)
  *C12N 15/63* (2006.01)

(52) U.S. Cl. ............... 435/455; 435/320.1; 435/325

(58) Field of Classification Search .............. None
  See application file for complete search history.

(56) References Cited

U.S. PATENT DOCUMENTS

| | | |
|---|---|---|
| 2009/0191159 A1 | 7/2009 | Sakurada et al. |
| 2010/0003757 A1 | 1/2010 | Mack et al. |

FOREIGN PATENT DOCUMENTS

| | | |
|---|---|---|
| WO | WO 2009/115295 A1 | 9/2009 |
| WO | WO 2009/133971 A1 | 11/2009 |
| WO | WO 2009/157201 A1 | 12/2009 |
| WO | WO 2010/012077 A1 | 2/2010 |

OTHER PUBLICATIONS

Yusa et al (Nature Method, 2009. vol. 6, No. 5, pp. 363-369).*
Jia, et al. A nonviral minicircle vector for deriving human iPS cells. Nat Methods. Mar. 2010;7(3):197-9.
Kaji, et al. Virus-free induction of pluripotency and subsequent excision of reprogramming factors. Nature. Apr. 9, 2009;458(7239):771-5.
Okita, et al. Generation of mouse induced pluripotent stem cells without viral vectors. Science. Nov. 7, 2008;322(5903):949-53.
Woltjen, et al. piggyBac transposition reprograms fibroblasts to induced pluripotent stem cells. Nature. Apr. 9, 2009;458(7239):766-70.
Yu, et al. Human induced pluripotent stem cells free of vector and transgene sequences. Science. May 8, 2009;324(5928):797-801.

* cited by examiner

*Primary Examiner* — Celine Qian
(74) *Attorney, Agent, or Firm* — Wilson, Sonsini, Goodrich & Rosati

(57) ABSTRACT

Provided herein are methods for generating human induced pluripotent stem cells free from genomic integration of exogenous transgenes by transfecting into nucleated blood cells one or more DNA expression vectors (e.g., plasmid vectors) that do not contain a mammalian origin of replication, and encode and permit expression of one or more reprogramming factors (e.g., Oct4, Sox2, Klf4, and c-Myc). Also provided herein are the integration-free human induced pluripotent stem cells obtained by the methods described herein.

5 Claims, 5 Drawing Sheets

SEQUENCE LISTING

<160> NUMBER OF SEQ ID NOS: 7

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcagtggag agggcagagg aagtctgcta acatgcggtg acgtcgagga gaatcctggc    60
cca                                                                 63

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggttctggcg tgaaacagac tttgaatttt gaccttctca gttggcggg agacgtggag    60 tccaacccag ggccc                                                    75

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Gly Val Lys Gln Thr Asn Phe Asp Leu Leu Lys Leu Ala Gly
1               5                   10                  15

Asp Val Glu Ser Asn Pro Gly Pro
            20

<210> SEQ ID NO 5
<211> LENGTH: 4971
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcccctca acgtgaactt caccaacagg aactatgacc tcgactacga ctccgtacag    60

```
ccctatttca tctgcgacga ggaagagaat ttctatcacc agcaacagca gagcgagctg     120
cagccgcccg cgcccagtga ggatatctgg aagaaattcg agctgcttcc caccccgccc     180
ctgtccccga gccgccgctc cgggctctgc tctccatcct atgttgcggt cgctacgtcc     240
ttctccccaa gggaagacga tgacggcggc ggtggcaact tctccaccgc cgatcagctg     300
gagatgatga ccgagttact tggaggagac atggtgaacc agagcttcat ctgcgatcct     360
gacgacgaga ccttcatcaa gaacatcatc atccaggact gtatgtggag cggtttctca     420
gccgctgcca agctggtctc ggagaagctg gcctcctacc aggctgcgcg caaagacagc     480
accagcctga gccccgcccg cgggcacagc gtctgctcca cctccagcct gtacctgcag     540
gacctcaccg ccgccgcgtc cgagtgcatt gaccectcag tggtctttcc ctacccgctc     600
aacgacagca gctcgcccaa atcctgtacc tcgtccgatt ccacggcctt ctctccttcc     660
tcggactcgc tgctgtcctc cgagtcctcc ccacgggcca gccctgagcc cctagtgctg     720
catgaggaga caccgcccac caccagcagc gactctgaag aagagcaaga agatgaggaa     780
gaaattgatg tggtgtctgt ggagaagagg caaaccectg ccaagaggtc ggagtcgggc     840
tcatctccat cccgaggcca cagcaaacct ccgcacagcc cactggtcct caagaggtgc     900
cacgtctcca ctcaccagca caactacgcc gcacccccct ccacaaggaa ggactatcca     960
gctgccaaga gggccaagtt ggacagtggc agggtcctga agcagatcag caacaaccgc    1020
aagtgctcca gccccaggtc ctcagacacg gaggaaaacg acaagaggcg gacacacaac    1080
gtcttggaac gtcagaggag gaacgagctg aagcgcagct ttttgccct gcgtgaccag    1140 atccctgaat tggaaaacaa cgaaaaggcc cccaaggtag tgatcctcaa aaaagccacc    1200
gcctacatcc tgtccattca gcagacgag cacaagctca cctctgaaaa ggacttattg    1260
aggaaacgac gagaacagtt gaaacacaaa ctcgaacagc ttcgaaactc tggtgcaggt    1320
tctggcgtga acagacttt gaattttgac cttctcaagt tggcgggaga cgtggagtcc    1380
aacccagggc ccatggctgt cagcgacgct ctgctcccgt ccttctccac gttcgcgtcc    1440
ggcccggcgg gaagggagaa gacactgcgt ccagcaggtg ccccgactaa ccgttggcgt    1500
gaggaactct ctcacatgaa gcgacttccc ccacttcccg gccgcccta cgacctggcg    1560 gcgacggtgg ccacagacct ggagagtggc ggagctggtg cagcttgcag cagtaacaac    1620
ccggccctcc tagcccggag ggagaccgag gagttcaacg acctcctgga cctagacttt    1680
atcctttcca actcgctaac ccaccaggaa tcggtggccg ccaccgtgac cacctcggcg    1740
tcagcttcat cctcgtcttc cccagcgagc agcggccctg ccagcgcgcc ctccacctgc    1800
agcttcagct atccgatccg ggccgggggt gacccgggcg tggctgccag caacacaggt    1860
ggagggctcc tctacagccg agaatctgcg ccacctccca cggcccectt caacctggcg    1920 gacatcaatg acgtgagccc ctcgggcggc ttcgtggctg agctcctgcg gccggagttg    1980
gacccagtat acattccgcc acagcagcct cagccgccag gtggcgggct gatgggcaag    2040
tttgtgctga aggcgtctct gaccacccct ggcagcgagt acagcagccc ttcggtcatc    2100
agtgttagca aaggaagccc agacggcagc caccccgtgg tagtggcgcc ctacagcggt    2160
ggcccgccgc gcatgtgccc caagattaag caagaggcgg tccgtcctg cacggtcagc    2220 cggtccctag aggcccattt gagcgctgga ccccagctca gcaacggcca ccggcccaac    2280
acacacgact tcccctggg gcggcagctc ccaccaggaa ctacccctac actgagtccc    2340
gaggaactgc tgaacagcag ggactgtcac cctggcctgc ctcttccccc aggattccat    2400
ccccatccgg ggcccaacta ccctccttc ctgccagacc agatgcagtc acaagtcccc    2460
```

```
tctctccatt atcaagagct catgccaccg ggttcctgcc tgccagagga gcccaagcca    2520
aagaggggaa gaaggtcgtg gccccggaaa agaacagcca cccacacttg tgactatgca    2580
ggctgtggca aaacctatac caagagttct catctcaagg cacacctgcg aactcacaca    2640
ggcgagaaac cttaccactg tgactgggac ggctgtgggt ggaaattcgc ccgctccgat    2700
gaactgacca ggcactaccg caaacacaca gggcaccggc cctttcagtg ccagaagtgc    2760
gacagggcct tttccaggtc ggaccacctt gccttacaca tgaagaggca ctttggctcc    2820
ggagagggca gaggaagtct gctaacatgc ggtgacgtcg aggagaatcc tgcccactc    2880 gagatggctg gacacctggc ttcagacttc gcctcctcac ccccaccagg tgggggtgat    2940
gggtcagcag ggctggagcc gggctgggtg gattctcgaa cctggctaag cttccaaggg    3000
cctccaggtg ggcctggaat cggaccaggc tcagaggtat tggggatctc cccatgtccg    3060
cccgcatacg agttctgcgg agggatggca tactgtggac ctcaggttgg actgggccta    3120
gtcccccaag ttggcgtgga gactttgcag cctgagggcc aggcaggagc acgagtggaa    3180
agcaactcag agggaacctc ctctgagccc tgtgccgacc gccccaatgc cgtgaagttg    3240
gagaaggtgg aaccaactcc cgaggagtcc caggacatga aagccctgca gaaggagcta    3300
gaacagtttg ccaagctgct gaagcagaag aggatcacct ggggtacac ccaggccgac    3360 gtggggctca ccctgggcgt tctctttgga aaggtgttca gccagaccac catctgtcgc    3420
ttcgaggcct gcagctcag ccttaagaac atgtgtaagc tgcggcccct gctggagaag    3480
tgggtggagg aagccgacaa caatgagaac cttcaggaga tatgcaaatc ggagaccctg    3540
gtgcaggccc ggaagagaaa gcgaactagc attgagaacc gtgtgaggtg gagtctggag    3600
accatgtttc tgaagtgccc gaagccctcc ctacagcaga tcactcacat cgccaatcag    3660
cttgggctag agaaggatgt ggttcgagta tggttctgta accggcgcca gaagggcaaa    3720
agatcaagta ttgagtattc ccaacgagaa gagtatgagg ctacagggac acctttccca    3780
gggggggctg tatccttttcc tctgcccccca ggtccccact ttggcacccc aggctatgga    3840
agcccccact tcaccacact ctactcagtc ccttttcctg agggcgaggc ctttccctct    3900
gttcccgtca ctgctctggg ctctcccatg cattcaaacg ggtcgggtca atgtactaac    3960
tacgctttgt tgaaactcgc tggcgatgtt gaaagtaata accccggtcc tatgtataac    4020
atgatggaga cggagctgaa gccgccgggc ccgcagcaag cttcgggggg cggcggcgga    4080
ggaggcaacg ccacggcggc ggcgaccggc ggcaaccaga agaacagccc ggaccgcgtc    4140
aagaggccca tgaacgcctt catggtatgg tcccggggc agcggcgtaa gatggcccag    4200
gagaacccca agatgcacaa ctcggagatc agcaagcgcc tgggcgcgga gtggaaactt    4260
ttgtccgaga ccgagaagcg gccgttcatc gacgaggcca gcggctgcg cgctctgcac    4320 atgaaggagc acccgggatta taaataccgg ccgcggcgga aaaccaagac gctcatgaag    4380
aaggataagt acacgcttcc cggaggcttg ctggcccccg gcgggaacag catggcgagc    4440
ggggttgggg tggcgccgg cctggttggc gggctgaacc agcgcatgga cagctacgcg    4500
cacatgaacg gctggagcaa cggcagctac agcatgatgc aggagcagct gggctacccg    4560
cagcacccgg gctcaacgc tcacggcgcg gcacagatgc aaccgatgca ccgctacgtc    4620
gtcagcgccc tgcagtacaa ctccatgacc agctcgcaga cctacatgaa cggctcgccc    4680
acctacagca tgtcctactc gcagcagggc acccccggta tggcgctggg ctccatgggc    4740
tctgtggtca agtccgaggc cagctccagc cccccgtgg ttacctcttc ctcccactcc    4800
agggcgccct gccaggccgg ggacctccgg gacatgatca gcatgtacct ccccggcgcc    4860
```

```
gaggtgccgg agcccgctgc gcccagtaga ctgcacatgg cccagcacta ccagagcggc    4920
ccggtgcccg gcacggccaa atacggcaca ctgcccctgt cgcacatgtg a             4971
```

<210> SEQ ID NO 6
<211> LENGTH: 1656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Glu Asn Phe Tyr
                20                  25                  30

His Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
```

```
                    340                 345                 350
Asn Asp Lys Arg Arg Thr His Asn Val Leu Glu Arg Gln Arg Arg Asn
                355                 360                 365
Glu Leu Lys Arg Ser Phe Phe Ala Leu Arg Asp Gln Ile Pro Glu Leu
            370                 375                 380
Glu Asn Asn Glu Lys Ala Pro Lys Val Val Ile Leu Lys Lys Ala Thr
385                 390                 395                 400
Ala Tyr Ile Leu Ser Ile Gln Ala Asp Glu His Lys Leu Thr Ser Glu
                405                 410                 415
Lys Asp Leu Leu Arg Lys Arg Glu Gln Leu Lys His Lys Leu Glu
            420                 425                 430
Gln Leu Arg Asn Ser Gly Ala Gly Ser Gly Val Lys Gln Thr Leu Asn
            435                 440                 445
Phe Asp Leu Leu Lys Leu Ala Gly Asp Val Glu Ser Asn Pro Gly Pro
        450                 455                 460
Met Ala Val Ser Asp Ala Leu Leu Pro Ser Phe Ser Thr Phe Ala Ser
465                 470                 475                 480
Gly Pro Ala Gly Arg Glu Lys Thr Leu Arg Pro Ala Gly Ala Pro Thr
                485                 490                 495
Asn Arg Trp Arg Glu Glu Leu Ser His Met Lys Arg Leu Pro Pro Leu
            500                 505                 510
Pro Gly Arg Pro Tyr Asp Leu Ala Ala Thr Val Ala Thr Asp Leu Glu
            515                 520                 525
Ser Gly Gly Ala Gly Ala Ala Cys Ser Ser Asn Asn Pro Ala Leu Leu
        530                 535                 540
Ala Arg Arg Glu Thr Glu Glu Phe Asn Asp Leu Leu Asp Leu Asp Phe
545                 550                 555                 560
Ile Leu Ser Asn Ser Leu Thr His Gln Glu Ser Val Ala Ala Thr Val
                565                 570                 575
Thr Thr Ser Ala Ser Ala Ser Ser Ser Ser Pro Ala Ser Ser Gly
            580                 585                 590
Pro Ala Ser Ala Pro Ser Thr Cys Ser Phe Ser Tyr Pro Ile Arg Ala
            595                 600                 605
Gly Gly Asp Pro Gly Val Ala Ala Ser Asn Thr Gly Gly Gly Leu Leu
        610                 615                 620
Tyr Ser Arg Glu Ser Ala Pro Pro Thr Ala Pro Phe Asn Leu Ala
625                 630                 635                 640
Asp Ile Asn Asp Val Ser Pro Ser Gly Gly Phe Val Ala Glu Leu Leu
                645                 650                 655
Arg Pro Glu Leu Asp Pro Val Tyr Ile Pro Pro Gln Gln Pro Gln Pro
            660                 665                 670
Pro Gly Gly Gly Leu Met Gly Lys Phe Val Leu Lys Ala Ser Leu Thr
        675                 680                 685
Thr Pro Gly Ser Glu Tyr Ser Ser Pro Ser Val Ile Ser Val Ser Lys
            690                 695                 700
Gly Ser Pro Asp Gly Ser His Pro Val Val Ala Pro Tyr Ser Gly
705                 710                 715                 720
Gly Pro Pro Arg Met Cys Pro Lys Ile Lys Gln Glu Ala Val Pro Ser
                725                 730                 735
Cys Thr Val Ser Arg Ser Leu Glu Ala His Leu Ser Ala Gly Pro Gln
            740                 745                 750
Leu Ser Asn Gly His Arg Pro Asn Thr His Asp Phe Pro Leu Gly Arg
        755                 760                 765
```

-continued

```
Gln Leu Pro Thr Arg Thr Thr Pro Thr Leu Ser Pro Glu Leu Leu
    770                 775                 780

Asn Ser Arg Asp Cys His Pro Gly Leu Pro Leu Pro Pro Gly Phe His
785                 790                 795                 800

Pro His Pro Gly Pro Asn Tyr Pro Pro Phe Leu Pro Asp Gln Met Gln
                805                 810                 815

Ser Gln Val Pro Ser Leu His Tyr Gln Glu Leu Met Pro Pro Gly Ser
            820                 825                 830

Cys Leu Pro Glu Glu Pro Lys Pro Lys Arg Gly Arg Arg Ser Trp Pro
        835                 840                 845

Arg Lys Arg Thr Ala Thr His Thr Cys Asp Tyr Ala Gly Cys Gly Lys
    850                 855                 860

Thr Tyr Thr Lys Ser Ser His Leu Lys Ala His Leu Arg Thr His Thr
865                 870                 875                 880

Gly Glu Lys Pro Tyr His Cys Asp Trp Asp Gly Cys Gly Trp Lys Phe
                885                 890                 895

Ala Arg Ser Asp Glu Leu Thr Arg His Tyr Arg Lys His Thr Gly His
            900                 905                 910

Arg Pro Phe Gln Cys Gln Lys Cys Asp Arg Ala Phe Ser Arg Ser Asp
        915                 920                 925

His Leu Ala Leu His Met Lys Arg His Phe Gly Ser Gly Glu Gly Arg
    930                 935                 940

Gly Ser Leu Leu Thr Cys Gly Asp Val Glu Glu Asn Pro Gly Pro Leu
945                 950                 955                 960

Glu Met Ala Gly His Leu Ala Ser Asp Phe Ala Ser Ser Pro Pro Pro
                965                 970                 975

Gly Gly Gly Asp Gly Ser Ala Gly Leu Glu Pro Gly Trp Val Asp Ser
            980                 985                 990

Arg Thr Trp Leu Ser Phe Gln Gly Pro Pro Gly Gly Pro Gly Ile Gly
        995                 1000                1005

Pro Gly Ser Glu Val Leu Gly Ile Ser Pro Cys Pro Pro Ala Tyr
    1010                1015                1020

Glu Phe Cys Gly Gly Met Ala Tyr Cys Gly Pro Gln Val Gly Leu
    1025                1030                1035

Gly Leu Val Pro Gln Val Gly Val Glu Thr Leu Gln Pro Glu Gly
    1040                1045                1050

Gln Ala Gly Ala Arg Val Glu Ser Asn Ser Glu Gly Thr Ser Ser
    1055                1060                1065

Glu Pro Cys Ala Asp Arg Pro Asn Ala Val Lys Leu Glu Lys Val
    1070                1075                1080

Glu Pro Thr Pro Glu Glu Ser Gln Asp Met Lys Ala Leu Gln Lys
    1085                1090                1095

Glu Leu Glu Gln Phe Ala Lys Leu Leu Lys Gln Lys Arg Ile Thr
    1100                1105                1110

Leu Gly Tyr Thr Gln Ala Asp Val Gly Leu Thr Leu Gly Val Leu
    1115                1120                1125

Phe Gly Lys Val Phe Ser Gln Thr Thr Ile Cys Arg Phe Glu Ala
    1130                1135                1140

Leu Gln Leu Ser Leu Lys Asn Met Cys Lys Leu Arg Pro Leu Leu
    1145                1150                1155

Glu Lys Trp Val Glu Glu Ala Asp Asn Asn Glu Asn Leu Gln Glu
    1160                1165                1170

Ile Cys Lys Ser Glu Thr Leu Val Gln Ala Arg Lys Arg Lys Arg
    1175                1180                1185
```

```
Thr Ser Ile Glu Asn Arg Val Arg Trp Ser Leu Glu Thr Met Phe
    1190            1195                1200

Leu Lys Cys Pro Lys Pro Ser Leu Gln Gln Ile Thr His Ile Ala
    1205            1210                1215

Asn Gln Leu Gly Leu Glu Lys Asp Val Arg Val Trp Phe Cys
    1220            1225                1230

Asn Arg Arg Gln Lys Gly Lys Arg Ser Ser Ile Glu Tyr Ser Gln
    1235            1240                1245

Arg Glu Glu Tyr Glu Ala Thr Gly Thr Pro Phe Pro Gly Gly Ala
    1250            1255                1260

Val Ser Phe Pro Leu Pro Pro Gly Pro His Phe Gly Thr Pro Gly
    1265            1270                1275

Tyr Gly Ser Pro His Phe Thr Thr Leu Tyr Ser Val Pro Phe Pro
    1280            1285                1290

Glu Gly Glu Ala Phe Pro Ser Val Pro Val Thr Ala Leu Gly Ser
    1295            1300                1305

Pro Met His Ser Asn Gly Ser Gly Gln Cys Thr Asn Tyr Ala Leu
    1310            1315                1320

Leu Lys Leu Ala Gly Asp Val Glu Ser Asn Asn Pro Gly Pro Met
    1325            1330                1335

Tyr Asn Met Met Glu Thr Glu Leu Lys Pro Pro Gly Pro Gln Gln
    1340            1345                1350

Ala Ser Gly Gly Gly Gly Gly Gly Asn Ala Thr Ala Ala Ala
    1355            1360                1365

Thr Gly Gly Asn Gln Lys Asn Ser Pro Asp Arg Val Lys Arg Pro
    1370            1375                1380

Met Asn Ala Phe Met Val Trp Ser Arg Gly Gln Arg Arg Lys Met
    1385            1390                1395

Ala Gln Glu Asn Pro Lys Met His Asn Ser Glu Ile Ser Lys Arg
    1400            1405                1410

Leu Gly Ala Glu Trp Lys Leu Leu Ser Glu Thr Glu Lys Arg Pro
    1415            1420                1425

Phe Ile Asp Glu Ala Lys Arg Leu Arg Ala Leu His Met Lys Glu
    1430            1435                1440

His Pro Asp Tyr Lys Tyr Arg Pro Arg Arg Lys Thr Lys Thr Leu
    1445            1450                1455

Met Lys Lys Asp Lys Tyr Thr Leu Pro Gly Gly Leu Leu Ala Pro
    1460            1465                1470

Gly Gly Asn Ser Met Ala Ser Gly Val Gly Val Gly Ala Gly Leu
    1475            1480                1485

Gly Gly Gly Leu Asn Gln Arg Met Asp Ser Tyr Ala His Met Asn
    1490            1495                1500

Gly Trp Ser Asn Gly Ser Tyr Ser Met Met Gln Glu Gln Leu Gly
    1505            1510                1515

Tyr Pro Gln His Pro Gly Leu Asn Ala His Gly Ala Ala Gln Met
    1520            1525                1530

Gln Pro Met His Arg Tyr Val Val Ser Ala Leu Gln Tyr Asn Ser
    1535            1540                1545

Met Thr Ser Ser Gln Thr Tyr Met Asn Gly Ser Pro Thr Tyr Ser
    1550            1555                1560

Met Ser Tyr Ser Gln Gln Gly Thr Pro Gly Met Ala Leu Gly Ser
    1565            1570                1575

Met Gly Ser Val Val Lys Ser Glu Ala Ser Ser Ser Pro Pro Val
```

-continued

```
              1580                1585                1590
Val Thr Ser Ser Ser His Ser Arg Ala Pro Cys Gln Ala Gly Asp
    1595                1600                1605

Leu Arg Asp Met Ile Ser Met Tyr Leu Pro Gly Ala Glu Val Pro
    1610                1615                1620

Glu Pro Ala Ala Pro Ser Arg Leu His Met Ala Gln His Tyr Gln
    1625                1630                1635

Ser Gly Pro Val Pro Gly Thr Ala Lys Tyr Gly Thr Leu Pro Leu
    1640                1645                1650

Ser His Met
    1655

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 7

Asp Xaa Glu Xaa Asn Pro Gly Pro
1               5
```

INTEGRATION-FREE HUMAN INDUCED PLURIPOTENT STEM CELLS FROM BLOOD

BACKGROUND OF THE INVENTION

The advent of cellular reprogramming technology to generate human induced pluripotent stem (hiPS) cells combined with directed differentiation in vitro has opened the door to vast opportunities for more effective drug discovery and regenerative medicine. Typically, an hiPS cell line is generated by transducing fibroblasts expanded from a small skin biopsy with one or more integrating retroviruses encoding reprogramming factors. The resulting hiPS line contains one or more proviral integrations, which may interfere with the use of the hiPS cell lines in several applications including, for example, regenerative medicine applications. Further, use of skin fibroblasts for generating hiPS cells presents a number of disadvantages: isolation of a skin biopsy is somewhat invasive for the patient; expansion of fibroblasts from a skin biopsy prior to cellular reprogramming is relatively slow and inefficient; and skin is often directly exposed to environmental mutagens (e.g., UV irradiation) that may compromise the genomic integrity of the fibroblasts and therefore that of fibroblast-derived hiPS cell lines.

SUMMARY OF THE INVENTION

Described herein are human induced pluripotent stem (hiPS) cells generated from nucleated blood cells and free from genomically integrated exogenous nucleic acid sequences ("integration-free" hiPS cells), as well as methods for generating such hiPS cells by using non-viral nucleic acid expression vectors (e.g., plasmid expression vectors).

Accordingly, in one aspect provided herein is a method for generating integration-free human induced pluripotent stem cells that includes transfecting human nucleated blood cells with one or more DNA expression vectors encoding reprogramming factors (a) Oct4, Sox2, Klf4, and c-Myc; (b) Oct4, Sox2, and Klf4; (c) Oct4, Sox2, Klf4, c-Myc, and Nanog; or (d) Oct 4, Sox2, Lin-28, and Nanog, expressing the encoded reprogramming factors in the transfected nucleated blood cells, and culturing the transfected nucleated blood cells under conditions adapted to growth of human induced pluripotent stem cells, and identifying integration-free human induced pluripotent stem cells that do not comprise exogenous DNA from the one or more nucleic acid expression vectors, wherein the transfected human nucleated blood cells do not express an exogenous trans-acting factor that binds to a replication origin of an extra-chromosomal template. In some embodiments, the one or more DNA expression vectors encode the reprogramming factors consisting of Oct4, Sox2, Klf4, and c-Myc. In some embodiments, tIn other embodiments, the one or more DNA expression vectors encode the reprogramming factors Oct4, Sox2, Klf4, c-Myc, and Nanog. In some embodiments, the one or more DNA expression vectors encode reprogramming factors consisting of Oct4, Sox2, Klf4, c-Myc, and Nanog. In other embodiments, the one or more DNA expression vectors encode reprogramming factors consisting of Oct4, Sox2, and Klf4. In some embodiments, the one or more DNA expression vectors do not comprise a mammalian origin of replication.

In some embodiments, the transfection is performed within a single 24 hour period. In other embodiments, the transfection is performed only one time. In some embodiments, the transfection comprises transfecting the nucleated blood cells with only one transfection method.

In some embodiments, the human peripheral blood is from an adult. In some embodiments, the transfection is done by electroporation, nucleofection, or lipofection. In one embodiment, the transfection is done by electroporation. In some embodiments, the DNA expression vector is a plasmid vector. In some embodiments, the one or more DNA expression vectors comprise two DNA expression vectors.

In some embodiments, the method does not include introducing or expressing a recombinase (e.g., Cre recombinase) or transposase (e.g., PiggyBac transposase or Sleeping Beauty transposase) in hiPS cells following the identification of hiPS cell colonies. In some embodiments, the method does not include a DNA expression vector excision step to generate the integration-free human induced pluripotent stem cells.

In some embodiments, the nucleated blood cells are not hematopoietic stem cells.

In some embodiments, the method includes transfecting the nucleated blood cells with a single DNA expression vector. In some embodiments, the one or more DNA expression vectors further encode a reporter protein (e.g., a fluorescent protein, β-lactamase, or a luciferase) that is expressed in the transfected nucleated blood cells. In some embodiments, where the one or more DNA expression vectors further encode a reporter protein, the identification step includes identifying human induced pluripotent stem colonies that do not express the reporter protein.

In some embodiments, the one or more DNA expression vectors encoding reprogramming factors do not encode Tert or SV40 Large T-antigen.

In a related aspect provided herein is an integration-free human iPS cell induced by transfecting nucleated blood cells from human peripheral blood with one or more DNA expression vectors encoding reprogramming factors (a) Oct4, Sox2, Klf4, and c-Myc; (b) Oct4, Sox2, and Klf4; (c) Oct4, Sox2, Klf4, c-Myc, and Nanog; or (d) Oct 4, Sox2, Lin-28, and Nanog, expressing the encoded reprogramming factors in the transfected nucleated blood cells, and culturing the transfected nucleated blood cells under conditions adapted to growth of human induced pluripotent stem cells, and identifying integration-free human induced pluripotent stem cells that do not comprise exogenous DNA from the one or more nucleic acid expression vectors, wherein the one or more DNA expression vectors do not contain a functional mammalian origin of replication. In some embodiments, the one or more DNA expression vectors encode the reprogramming factors Oct4, Sox2, Klf4, and c-Myc. In some embodiments, the just-mentioned integration-free human induced pluripotent stem cell comprises a rearrangement in the Vj immunoglobulin genomic locus (e.g., VJ or VDJ recombination in the heavy and/or light chain locus) or a rearrangement of the T-cell receptor genomic locus (e.g., VJ or VDJ recombination in the alpha and/or beta chain locus). In some embodiments, the just-mentioned integration-free human induced pluripotent stem cell comprises a rearrangement in the VJ region of the immunoglobulin genomic locus. In some embodiments, the just-mentioned integration-free human induced pluripotent stem cell comprises somatic hypermutation in the immunoglobulin genomic locus. In some embodiments, the just-mentioned integration-free human induced pluripotent stem cell comprises a genomic change commonly associated with a B cell or T cell (e.g., junctional diversity, somatic recombination, somatic hypermutation).

INCORPORATION BY REFERENCE

All publications and patent applications mentioned in this specification are herein incorporated by reference to the same

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Introduction

Figure 1:
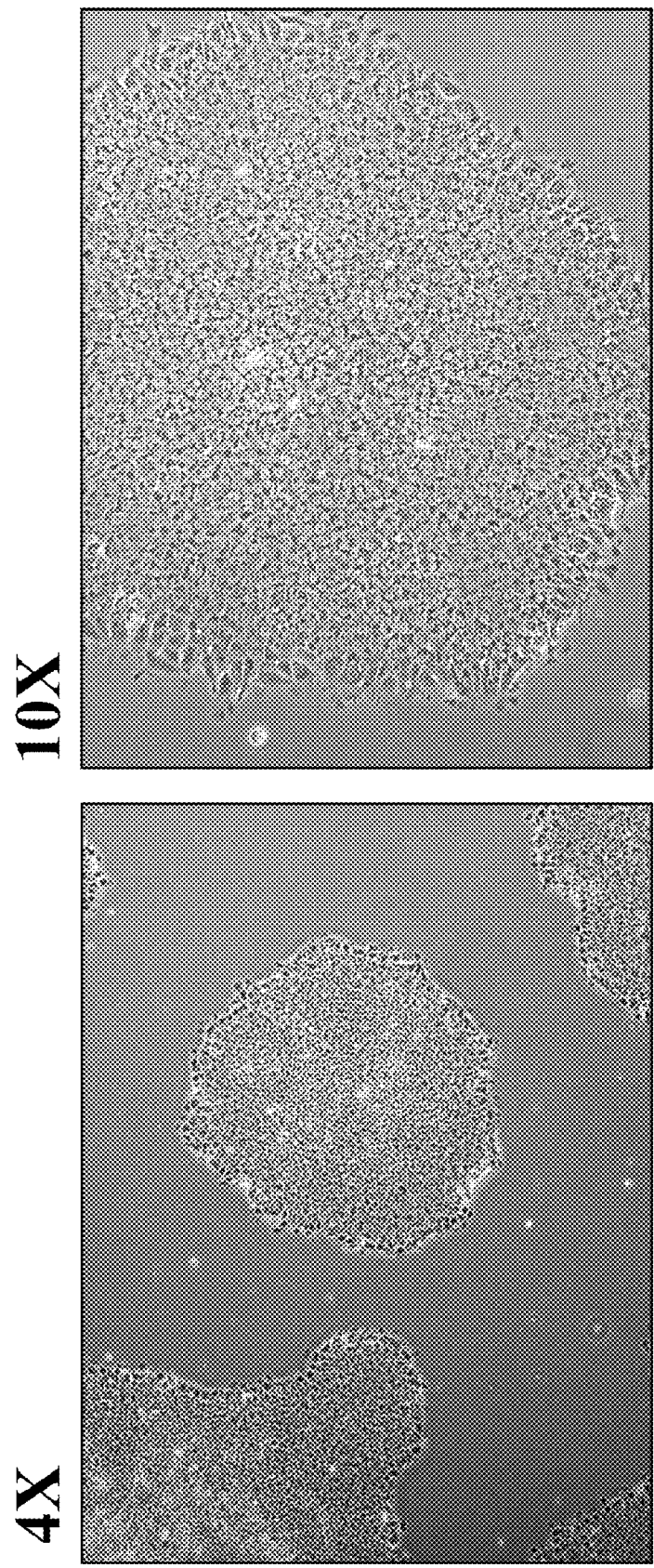
FIG. 1 shows a pair of photomicrographs (at 4× and 10× magnification) of individual colonies from the integration-free hiPS cell line 630.2, which was derived from adult nucleated blood cells by a single transient transfection with a plasmid encoding the reprogramming factors Oct4, Sox2, Klf4, and c-Myc.

Described herein are integration-free human induced pluripotent stem (hiPS) cells generated from nucleated blood cells and methods for generating such hiPS cells. These methods and compositions are based on the unexpected finding that human nucleated blood cells are, amenable to cellular reprogramming by transient transfection with virus-free nucleic acid expression vectors (e.g., plasmid expression vectors) that (i) encode reprogramming factors and permit their transient expression in human cells, and (ii) do not encode an exogenous trans-acting factor that binds to the replication origin to replicate an extra-chromosomal template. In some embodiments, cellular reprogramming of nucleated blood cells includes a single transient transfection of one or more nucleic acid vectors encoding reprogramming factors, or transfection of these one or more expression vectors during only a single 24 hour period. Without wishing to be bound by theory, it is believed that nucleated blood cells are more amenable to reprogramming by transient transfection because nucleated blood cells, in contrast to fibroblasts, have very limited proliferative potential in vitro, which thereby limits dilution/loss of transfected nucleic acid expression vectors in the transfected population over time, and allows transient expression of reprogramming factors at sufficiently high levels and for sufficiently long times to effect induction of hiPS cells.

II. Definitions

"transient transfection," as used herein, refers to the introduction of n exogenous nucleic acid into a mammalian cell by a method that does not generally result in the integration of the exogenous nucleic into the genome of the transiently transfected mammalian cell.

"mononucleated blood cells," as used herein, refers to any of B cell lymphocytes, T cell lymphocytes, neutrophils, eosinophils, basophils, monocytes, macrophages, dendritic cells, andcirculating hematopoietic stem cells.

"mammalian origin of replication," or "replication origin of an extra-chromosomal template," as used herein, refers to a nucleic acid sequence that permits episomal replication of a nucleic acid vector (e.g., a plasmid) in mammalian cells. Examples of a mammalian origin of replication include, but are not limited to, any of replication origin of a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV.

"reprogramming factor," as used herein, refers to any gene product, though usually a polypeptide, that alone or in combination with other reprogramming factors or reprogramming agents reprograms a postnatal somatic cell to become a pluripotent stem cell.

"induced pluripotent stem cell," as used herein, refers to a pluripotent stem cell derived from a postnatal somatic cell by any combination of forced expression of reprogramming factors alone or in combination with one or more reprogramming agents.

"nucleic acid expression vector," as used herein, refers to a nucleic acid not associated with viral proteins, competent to that encodes one or more proteins to be expressed in a host mammalian cell. In some cases, the nucleic acid expression vector is a DNA expression vector, e.g., a plasmid, a minicircle, a PCR product expression cassette, or a BAC. Such DNA expression vectors include a promoter, a polyadenylation sequence, a kozak initiation sequence that allow for transcription and translation of genes encoded by an expression cassette included within the nucleic acid vector sequence. In other cases, the nucleic acid expression vector is an RNA expression vector, i.e., a cRNA that encodes one or more proteins for expression in a host cell, and is competent for translation within the mammalian host cell.

"nucleated blood cell populations," "nucleated blood cells," or "NBCs," as used herein, refer to cells including any of the following cell types present in peripheral blood or cord blood: white blood cells, macrophages, monocytes, dendritic cells, lymphocytes, T-cells, B-cells, NK cells, granulocytes, basophils, eosinophils, neutrophils, and any progenitor cell thereof. The term NBC, as used herein, also refers to cells (e.g., macrophages, dendritic cells, etc.) derived from cells isolated from the blood (e.g., monocytes). For example, the term NBCs includes macrophages and/or dendritic cells obtained by in vitro or in vivo maturation or differentiation of monocytes present in, or purified from, peripheral blood obtained from a subject. The term NBC, as used herein, also refers to both mature and immature cells, e.g., mature or immature dendritic cells. A NBC "subpopulation" refers to an NBC population that has been specifically enriched for or depleted of any of the forgoing NBC types.

III. Methods

Overview

The methods described herein are drawn to generation of integration-free human iPS (hiPS) cells from nucleated blood cells (NBCs). In some cases, NBCs are isolated directly from a blood sample, transfected with one or more vectors for expression of one or more reprogramming factors, cultured in a medium suitable for human iPS cells (e.g., mTeSR medium), and then examined for the development of colonies exhibiting human pluripotent stem cell morphology and pluripotent gene expression patterns as described herein. In other cases, a NBC fraction is cultured prior to prior to reprogramming to enrich for or deplete particular cell types within the NBC population as described herein. Of note, the transfected human NBCs do not express an exogenous or endogenous trans-acting factor that binds to a replication origin of an extra-chromosomal template as is found in so-called "episomal vectors." See, e.g., Yu et al (2009), *Science*, 324(5928): 797-801. Such trans-acting factors include, but are not limited to, EBNA-1 of the Epstein-Barr Virus, large T antigen of a mouse polyomavirus, the large T antigen of a BK virus, E1 and E2 of a bovine papilloma virus, and Epstein-Barr Nuclear Antigen-1 (EBNA-1), and sequence variants of any of the foregoing that retain the ability to bind to their respective replication origin element, also referred to herein as a "mammalian origin of replication." Further, the methods described herein do not require an excision step (e.g., by expression of a recombinase or transposase) to remove transfected DNA expression vectors from the hiPS cells obtained by the reprogramming methods described herein.

Isolation of NBCs

In some embodiments, a nucleated blood cell fraction is obtained by the Ficoll-Hypaque method, as described in, e.g., Kanof et al., (1993), Current Protocols in Immunology (J. E. Coligan, A. M. Kruisbeek, D. H. Margulies, E. M. Shevack, and W. Strober, eds.), ch. 7.1.1.-7.1.5, John Wiley & Sons, New York). In some embodiments, the isolation of a nucleated blood cell fraction is performed on a human blood sample (peripheral blood or cord blood) volume of at least about 1 ml to about 50 ml, e.g., 3 ml, 7 ml, 8 ml, 10 ml, 12 ml, 15 ml, 20 ml, 25 ml, 30 ml, 35 ml, 37 ml, 40 ml, 42 ml, 45 ml, or another volume of peripheral blood or cord blood from at least about 1 ml to about 50 ml. For the methods described herein NBCs may be isolated from fresh whole blood samples; from whole blood (or NBC-containing blood fraction) samples stored for about two days to about five weeks in heparanized storage tubes; or from cryopreserved whole blood (or NBC-containing fraction) samples cryopreserved with DMSO in liquid nitrogen by standard methods (see, e.g., Stevens et al (2007), *Cancer Epidemiol Biomarkers Prev,* 16(10):2160-2163.

In some cases, reprogramming is performed on NBC subpopulations that are depleted of or enriched in certain cell types. Specific cell populations can be depleted or enriched using standard methods. For example, monocytes/macrophages can be isolated by differential adherence on plastic. T cells, B cells, macrophages, and granulocytes can be enriched or depleted, for example, by positive and/or negative selection using antibodies to cell type-specific surface markers. Examples of suitable cell type-specific surface marker proteins for which antibodies commonly used for selection or depletion of specific NBC subpopulations, include, but are not limited to CD3 for T cells, CD19 for B cells, CD14 for monocytes/macrophages and CD 15 for granulocytes. Specific cell populations can be enriched or depleted by incubating cells with a specific primary monoclonal antibody (mAb), followed by isolation of cells that bind the mAb by a number of well known methods including fluorescence-activated cell sorting (FACS), magnetic bead sorting, or magnetic-activated cell sorting (MACST™).

In some cases, NBCs are depleted of particular cell types by negative selection, where the NBCs are incubated in the presence of one or more antibodies against cell surface markers specific to the undesired cell types. Afterwards, the labeled subpopulation of cells is depleted (negative selection) from the NBC sample by any of the above-mentioned methods, e.g., FACS. In some embodiments, NBCs are depleted of B cells and T cells by incubating NBCs in the presence of antibodies against CD3 (for T-cells) and CD19 (for B cells) and selecting cells, e.g., by FACS, that are not labeled by such antibodies.

In other cases, specific cell types, e.g., T-cells, are isolated by incubating NBCs in the presence of antibodies against cell surface markers specific to the desired cell types. Afterwards, the labeled subpopulation of cells is selected (positive selection) from the NBC sample by any of the above-mentioned methods, e.g., FACS. In some embodiments, monocytes/macrophages and/or granulocytes are selected by incubating NBCs in the presence of CD14 and CD15 antibodies, respectively, and then isolating the labeled cells by FACS or other another suitable method as described herein or known in the art.

In some cases NBCs are first subjected to a round of negative selection to deplete one or more cell types (e.g., B-cells and T-cells), and the remaining cell population is then subjected to positive selection to isolate specific cell types (monocytes/macrophages or granulocytes). In other embodiments, positive selection is performed first on the NBCs, and then followed by negative selection of the positively selected cell population to deplete the positively selected cell population of unwanted cell types.

In some embodiments, a NBC fraction is subjected to positive selection with antibodies against CD14 and CD15, followed by FACS or MACS for isolation of $CD14^+$ or $CD15^+$ cells. In other embodiments, MACS is used to isolate $CD14^+$ or $CD15^+$ cells. In some embodiments, the isolated CD14+ cells are further differentiated into macrophages or dendritic cells.

In other cases, a NBC fraction is subjected to negative selection with antibodies against CD3 and CD19, followed by FACS or MACS for isolation of $CD3^-$ and $CD19^-$ cells.

In some embodiments, PBNCs or a subpopulation of PBNCs are cultured prior to reprogramming by the methods described herein. In some cases, culture conditions are selected that favor selective proliferation of some cell types from a starting population of PBNCs. For example, where selective proliferation of cells of myeloid lineage is preferred, culture of NBCs is carried out in the presence of GM-CSF, G-CSF, IL-4, SCF alone or in combination. Examples of suitable culture conditions can be found for macrophages in U.S. Pat. No. 5,078,996, neutrophils/granulocytes in U.S. patent publication No. 20030039661, or dendritic cells in U.S. Pat. No. 5,851,756.

In some embodiments, the NBCs to be reprogrammed by the methods described herein do not include hematopoietic stem cells.

The NBCs can be derived from neonatal or postnatal blood collected from a subject within the period from birth, including cesarean birth, to death. For example, the tissue may be from a subject who is >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months, or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years old.

The NBCs may be collected from subjects with a variety of disease statuses. The cells can be collected from a subject who is free of an adverse health condition. In other cases, the subject is suffering from, or at high risk of suffering from, a disease or disorder, e.g., a chronic health condition such as cardiovascular disease, eye disease (e.g., macular degeneration), auditory disease, (e.g., deafness), diabetes, obesity, cognitive impairment, schizophrenia, depression, bipolar disorder, dementia, neurodegenerative disease, Spinal Muscular Atrophy, Alzheimer's Disease, Parkinson's Disease, Huntington's Disease, multiple sclerosis, osteoporosis, liver disease, kidney disease, autoimmune disease, arthritis, or a proliferative disorder (e.g., a cancer). In other cases, the subject is suffering from, or at high risk of suffering from, an acute health condition, e.g., stroke, spinal cord injury, burn, or a wound. In certain cases, a subject provides cells for his or her future use (e.g., an autologous therapy), or for the use of another subject who may need treatment or therapy (e.g., an allogeneic therapy). In some cases, the donor and the recipient are immunohistologically compatible or HLA-matched.

Reprogramming NBCs by Introduction of Nucleic Acid Vectors

Where DNA expression vectors are used, such vectors include a promoter competent to drive reprogramming factor gene transcription in a plurality of cells to be reprogrammed within an expression cassette encoding at least one reprogramming factor. In some embodiments, the DNA expression vectors used in the reprogramming methods described herein do not include loxP transposition target sites for CRE recombinase, or a mammalian origin of replication, e.g., the Epstein-Barr Virus oriP element (Yates et al (1984), *Proc. Natl. Acad. Sci. USA*, 81:3806-3810. Other examples of a mammalian origin of replication include, but are not limited to, replication origin of a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. With reference to a replication origin that may serve as a mammalian origin of replication, lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. DNA expression vectors comprising a mammalian origin of replication are capable of being stably replicated as extrachromosomal episomes even within cells that actively proliferate, e.g., fibroblasts in the presence of a sufficient level of serum. Examples of vectors comprising a mammalian origin of replication are described in, e.g., U.S. patent application Ser. No. 12/478, 154. In some embodiments, the DNA expression vectors suitable for the methods described herein do not contain the mammalian origin of replication found in, e.g., any of the following episomal vectors: pCEP4, pREP4, or pEBNA DEST. In some embodiments, the DNA expression vectors suitable for the methods described herein do not include a S/MAR (scaffold/matrix attachment region) sequence. See, e.g., Piechaczek et al (1999), *Nucleic Acids Res*, 27:426-428.

Examples of suitable promoters for driving mammalian cell expression of the polypeptides described herein in include, but are not limited to, constitutive promoters such as, CMV, CAG, EF-1α, HSV1-TK, SV40, EF-1α, β actin; PGK, and inducible promoters, such as those containing TET-operator elements. In certain embodiments, cell type-specific promoters are used to drive expression of reprogramming factors in specific cell types. Examples of suitable cell type-specific promoters useful for the methods described herein include, but are not limited to, the synthetic macrophage-specific promoter described in He et al (2006), *Human Gene Therapy,* 17:949-959; the granulocyte and macrophage-specific lysozyme M promoter (see, e.g., Faust et al (2000), *Blood,* 96(2):719-726); and the myeloid-specific CD11b promoter (see, e.g., Dziennis et al (1995), *Blood,* 85(2):319-329). In some cases, an expression cassette encodes a polycistronic mRNA (a "polycistronic expression cassette"), which, upon translation gives rise to independent polypeptides comprising different amino acid sequences or functionalities. In some embodiments, a polycistronic expression cassette encodes a "polyprotein" comprising multiple polypeptide sequences that are separated by encoded by a picornavirus, e.g., a foot-and-mouth disease virus (FMDV) viral 2A peptide sequence. The 2A peptide sequence acts co-translationally, by preventing the formation of a normal peptide bond between the conserved glycine and last proline, resulting in ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. which during translation allow cleavage of the nascent polypeptide sequence into separate polypeptides. See, e.g., Trichas et al (2008), *BMC Biol,* 6:40. Two exemplary 2A nucleotide sequences and their corresponding peptide sequences are shown below:

5'GGCAGTGGAGAGGGCAGAGGAAGTCT-
GCTAACATGCGGTGACGTCGAGGAGAAT
CCTGGCCCA3' (SEQ ID NO:1), which is translated into the peptide sequence:
GSGEGRGSLLTCGDVEENPGP (SEQ ID NO:2); or
5'GGTTCTGGCGTGAAACA-
GACTTTGAATTTTGACCTTCTCAAGTTG-
GCGGGA GACGTGGAGTCCAAC-
CCAGGGCCC3' (SEQ ID NO:3)
which translates to the sequence GSGVKQTN-FDLLKLAGDVESNPGP (SEQ ID NO: 4)

In other embodiments, a polycistronic expression cassette may incorporate one or more internal ribosomal entry site (IRES) sequences between open reading frames incorporated into the polycistronic expression cassette. IRES sequences and their use are known in the art as exemplified in, e.g., Martinez-Sales, *Curr Opin Biotechnol,* 10(5):458-464.

Reprogramming Factors

In various embodiments, nucleic acids encoding one or more reprogramming factors useful in cellular reprogramming of human NBCs into hiPS cells are used. Examples of suitable reprogramming factor genes include, but are not limited to genes encoding a polypeptide that comprises an amino acid sequence at least 80% identical, e.g., at least 85%, 88%, 90%, 95%, 97%, or another percent identical to the amino sequence of any of the following human or mouse sequences: Oct 4 (GenBank Accession Nos. NP_002692 and NP_038661.2, respectively), Sox2 (GenBank Accession Nos. NP_003097.1 and AAH57574, respectively), Klf4 (GenBank Accession Nos. NP_004226.3 and NP_034767.2, respectively), c-Myc (NP_002458.2 and NP_034979, respectively), Nanog (AY230262.1 and NP_082292.1, respectively), and Lin-28 (NP_078950.1 and NP_665832.1, respectively). In some embodiments, the encoded reprogramming factors may also include human or mouse activation-induced cytidine deaminase (AID), (GenBank Accession Nos. (NP_065712.1 and NP_033775.1, respectively). In some embodiments, the encoded reprogramming factor amino acid sequences are from human. In other embodiments, the encoded sequences are from mouse. In some embodiments, a nucleic acid expression vector encodes the human ortholog of any of Oct 4, Sox2, Klf4, c-Myc, Nanog, or Lin-28. In other embodiments, a nucleic acid expression vector encodes the mouse ortholog of any of Oct 4, Sox2, Klf4, c-Myc, Nanog, or Lin-28. In some embodiments, an expression cassette is a polycistronic expression cassette that encodes the amino acids sequences of multiple reprogramming factors, the expression of which is under the control of the same promoter. Such polycistronic expression cassettes may include at least two, three, four, five, or six reprogramming factors. In some cases, an expression cassette includes the open reading frames for Oct 4 and Sox2. In other cases, the expression cassette includes the open reading frames for Oct 4, Sox2, and Klf4. In other embodiments, the expression cassette includes the open reading frames for Oct 4, Sox2, Klf4, and c-Myc. In further embodiments, the expression cassette includes the open reading frames for Oct 4, Sox2, Nanog, and Lin-28. In some embodiments, a polycistronic expression cassette for expression of multiple reprogramming factors contains the sequence encoding the 2A peptide between the sequences encoding the various reprogramming factors. A polycistronic expression cassette may contain the sequences of reprogramming factors from 5' to 3' in any order. In some cases, a polycistronic expression cassette comprises a nucleic acid sequence encoding reprogramming factors in the order from 5' to 3' c-Myc, Kl4, Oct4, Sox2 with intervening 2A sequences (lower case) as shown in the following exemplary nucleotide and amino acid sequences:

```
ATGCCCCTCAACGTGAACTTCACCAACAGGAACTATGACCTCGACTAC

GACTCCGTACAGCCCTATTTCATCTGCGACGAGGAAGAGAATTTCTAT

CACCAGCAACAGCAGAGCGAGCTGCAGCCGCCCGCGCCCAGTGAGGAT

ATCTGGAAGAAATTCGAGCTGCTTCCCACCCCGCCCCTGTCCCCGAGC

CGCCGCTCCGGGCTCTGCTCTCCATCCTATGTTGCGGTCGCTACGTCC

TTCTCCCCAAGGGAAGACGATGACGGCGGCGGTGGCAACTTCTCCACC

GCCGATCAGCTGGAGATGATGACCGAGTTACTTGGAGGAGACATGGTG

AACCAGAGCTTCATCTGCGATCCTGACGACGAGACCTTCATCAAGAAC

ATCATCATCCAGGACTGTATGTGGAGCGGTTTCTCAGCCGCTGCCAAG

CTGGTCTCGGAGAAGCTGGCCTCCTACCAGGCTGCGCGCAAAGACAGC

ACCAGCCTGAGCCCCGCCCGCGGGCACAGCGTCTGCTCCACCTCCAGC

CTGTACCTGCAGGACCTCACCGCCGCCGCGTCCGAGTGCATTGACCCC

TCAGTGGTCTTTCCCTACCCGCTCAACGACAGCAGCTCGCCCAAATCC

TGTACCTCGTCCGATTCCACGGCCTTCTCTCCTTCCTCGGACTCGCTG

CTGTCCTCCGAGTCCTCCCCACGGGCCAGCCCTGAGCCCCTAGTGCTG

CATGAGGAGACACCGCCCACCACCAGCAGCGACTCTGAAGAAGAGCAA

GAAGATGAGGAAGAAATTGATGTGGTGTCTGTGGAGAAGAGGCAAACC

CCTGCCAAGAGGTCGGAGTCGGGCTCATCTCCATCCCGAGGCCACAGC

AAACCTCCGCACAGCCCACTGGTCCTCAAGAGGTGCCACGTCTCCACT

CACCAGCACAACTACGCCGCACCCCCCTCCACAAGGAAGGACTATCCA

GCTGCCAAGAGGGCCAAGTTGGACAGTGGCAGGGTCCTGAAGCAGATC
```

```
AGCAACAACCGCAAGTGCTCCAGCCCCAGGTCCTCAGACACGGAGGAA
AACGACAAGAGGCGGACACACAACGTCTTGGAACGTCAGAGGAGGAAC
GAGCTGAAGCGCAGCTTTTTTGCCCTGCGTGACCAGATCCCTGAATTG
GAAAACAACGAAAAGGCCCCCAAGGTAGTGATCCTCAAAAAAGCCACC
GCCTACATCCTGTCCATTCAAGCAGACGAGCACAAGCTCACCTCTGAA
AAGGACTTATTGAGGAAACGACGAGAACAGTTGAAACACAAACTCGAA
CAGCTTCGAAACTCTGGTGCAggttctggcgtgaaacagactttgaat
tttgaccttctcaagttggcgggagacgtggagtccaacccagggccc
ATGGCTGTCAGCGACGCTCTGCTCCCGTCCTTCTCCACGTTCGCGTCC
GGCCCGGCGGGAAGGGAGAAGACACTGCGTCCAGCAGGTGCCCCGACT
AACCGTTGGCGTGAGGAACTCTCTCACATGAAGCGACTTCCCCCACTT
CCCGGCCGCCCCTACGACCTGGCGGCGACGGTGGCCACAGACCTGGAG
AGTGGCGGAGCTGGTGCAGCTTGCAGCAGTAACAACCCGGCCCTCCTA
GCCCGGAGGGAGACCGAGGAGTTCAACGACCTCCTGGACCTAGACTTT
ATCCTTTCCAACTCGCTAACCCACCAGGAATCGGTGGCCGCCACCGTG
ACCACCTCGGCGTCAGCTTCATCCTCGTCTTCCCCAGCGAGCAGCGGC
CCTGCCAGCGCGCCCTCCACCTGCAGCTTCAGCTATCCGATCCGGGCC
GGGGGTGACCCGGGCGTGGCTGCCAGCAACACAGGTGGAGGGCTCCTC
TACAGCCGAGAATCTGCGCCACCTCCCACGGCCCCCTTCAACCTGGCG
GACATCAATGACGTGAGCCCCTCGGGCGGCTTCGTGGCTGAGCTCCTG
CGGCCGGAGTTGGACCCAGTATACATTCCGCCACAGCAGCCTCAGCCG
CCAGGTGGCGGGCTGATGGGCAAGTTTGTGCTGAAGGCGTCTCTGACC
ACCCCTGGCAGCGAGTACAGCAGCCCTTCGGTCATCAGTGTTAGCAAA
GGAAGCCCAGACGGCAGCCACCCCGTGGTAGTGGCGCCCTACAGCGGT
GGCCCGCCGCGCATGTGCCCCAAGATTAAGCAAGAGGCGGTCCCGTCC
TGCACGGTCAGCCGGTCCCTAGAGGCCCATTTGAGCGCTGGACCCCAG
CTCAGCAACGGCCACCGGCCCAACACACACGACTTCCCCCTGGGGCGG
CAGCTCCCCACCAGGACTACCCCTACACTGAGTCCCGAGGAACTGCTG
AACAGCAGGGACTGTCACCCTGGCCTGCCTCTTCCCCCAGGATTCCAT
CCCCATCCGGGGCCCAACTACCCTCCTTTCCTGCCAGACCAGATGCAG
TCACAAGTCCCCTCTCTCCATTATCAAGAGCTCATGCCACCGGGTTCC
TGCCTGCCAGAGGAGCCCAAGCCAAAGAGGGGAAGAAGGTCGTGGCCC
CGGAAAAGAACAGCCACCCACACTTGTGACTATGCAGGCTGTGGCAAA
ACCTATACCAAGAGTTCTCATCTCAAGGCACACCTGCGAACTCACACA
GGCGAGAAACCTTACCACTGTGACTGGGACGGCTGTGGGTGGAAATTC
GCCCGCTCCGATGAACTGACCAGGCACTACCGCAAACACACAGGGCAC
CGGCCCTTTCAGTGCCAGAAGTGCGACAGGGCCTTTTCCAGGTCGGAC
CACCTTGCCTTACACATGAAGAGGCACTTTggctccggagagggcaga
ggaagtctgctaacatgcggtgacgtcgaggagaatcctggcccactc
gagATGGCTGGACACCTGGCTTCAGACTTCGCCTCCTCACCCCCACCA
GGTGGGGGTGATGGGTCAGCAGGGCTGGAGCCGGGCTGGGTGGATTCT
```

```
CGAACCTGGCTAAGCTTCCAAGGGCCTCCAGGTGGGCCTGGAATCGGA
CCAGGCTCAGAGGTATTGGGGATCTCCCCATGTCCGCCCGCATACGAG
TTCTGCGGAGGGATGGCATACTGTGGACCTCAGGTTGGACTGGGCCTA
GTCCCCAAGTTGGCGTGGAGACTTTGCAGCCTGAGGGCCAGGCAGGA
GCACGAGTGGAAAGCAACTCAGAGGGAACCTCCTCTGAGCCCTGTGCC
GACCGCCCCAATGCCGTGAAGTTGGAGAAGGTGGAACCAACTCCCGAG
GAGTCCCAGGACATGAAAGCCCTGCAGAAGGAGCTAGAACAGTTTGCC
AAGCTGCTGAAGCAGAAGAGGATCACCTTGGGGTACACCCAGGCCGAC
GTGGGGCTCACCCTGGGCGTTCTCTTTGGAAAGGTGTTCAGCCAGACC
ACCATCTGTCGCTTCGAGGCCTTGCAGCTCAGCCTTAAGAACATGTGT
AAGCTGCGGCCCCTGCTGGAGAAGTGGGTGGAGGAAGCCGACAACAAT
GAGAACCTTCAGGAGATATGCAAATCGGAGACCCTGGTGCAGGCCCGG
AAGAGAAAGCGAACTAGCATTGAGAACCGTGTGAGGTGGAGTCTGGAG
ACCATGTTTCTGAAGTGCCCGAAGCCCTCCCTACAGCAGATCACTCAC
ATCGCCAATCAGCTTGGGCTAGAGAAGGATGTGGTTCGAGTATGGTTC
TGTAACCGGCGCCAGAAGGGCAAAAGATCAAGTATTGAGTATTCCCAA
CGAGAAGAGTATGAGGCTACAGGGACACCTTTCCCAGGGGGGCTGTA
TCCTTTCCTCTGCCCCCAGGTCCCCACTTTGGCACCCCAGGCTATGGA
AGCCCCCACTTCACCACACTCTACTCAGTCCCTTTTCCTGAGGGCGAG
GCCTTTCCCTCTGTTCCCGTCACTGCTCTGGGCTCTCCCATGCATTCA
AACgggtcgggtcaatgtactaactacgctttgttgaaactcgctggc
gatgttgaaagtaataaccccggtcctATGTATAACATGATGGAGACG
GAGCTGAAGCCGCCGGGCCCGCAGCAAGCTTCGGGGGGCGGCGGCGGA
GGAGGCAACGCCACGGCGGCGGCGACCGGCGGCAACCAGAAGAACAGC
CCGGACCGCGTCAAGAGGCCCATGAACGCCTTCATGGTATGGTCCCGG
GGGCAGCGGCGTAAGATGGCCCAGGAGAACCCCAAGATGCACAACTCG
GAGATCAGCAAGCGCCTGGGCGCGGAGTGGAAACTTTTGTCCGAGACC
GAGAAGCGGCCGTTCATCGACGAGGCCAAGCGGCTGCGCGCTCTGCAC
ATGAAGGAGCACCCGGATTATAAATACCGGCCGCGGCGGAAAACCAAG
ACGCTCATGAAGAAGGATAAGTACACGCTTCCCGGAGGCTTGCTGGCC
CCCGGCGGGAACAGCATGGCGAGCGGGGTTGGGGTGGGCGCCGGCCTG
GGTGGCGGGCTGAACCAGCGCATGGACAGCTACGCGCACATGAACGGC
TGGAGCAACGGCAGCTACAGCATGATGCAGGAGCAGCTGGGCTACCCG
CAGCACCCGGGCCTCAACGCTCACGGCGCGGCACAGATGCAACCGATG
CACCGCTACGTCGTCAGCGCCCTGCAGTACAACTCCATGACCAGCTCG
CAGACCTACATGAACGGCTCGCCCACCTACAGCATGTCCTACTCGCAG
CAGGGCACCCCGGTATGGCGCTGGGCTCCATGGGCTCTGTGGTCAAG
TCCGAGGCCAGCTCCAGCCCCCCCGTGGTTACCTCTTCCTCCCACTCC
AGGGCGCCCTGCCAGGCCGGGACCTCCGGGACATGATCAGCATGTAC
CTCCCCGGCGCCGAGGTGCCGGAGCCCGCTGCGCCCAGTAGACTGCAC
```

-continued
ATGGCCCAGCACTACCAGAGCGGCCCGGTGCCCGGCACGGCCAAATAC

GGCACACTGCCCCTGTCGCACATGTGA (SEQ ID NO: 5), which translates to the following amino acid sequence:

MPLNVNFTNRNYDLDYDSVQPYFICDEEENFYHQQQQSELQPPAPSE

DIWKKFELLPTPPLSPSRRSGLCSPSYVAVATSFSPREDDDGGGGNF

STADQLEMMTELLGGDMVNQSFICDPDDETFIKNIIIQDCMWSGFSA

AAKLVSEKLASYQAARKDSTSLSPARGHSVCSTSSLYLQDLTAAASE

CIDPSVVFPYPLNDSSSPKSCTSSDSTAFSPSSDSLLSSESSPRASP

EPLVLHEETPPTTSSDSEEEQEDEEEIDVVSVEKRQTPAKRSESGSS

PSRGHSKPPHSPLVLKRCHVSTHQHNYAAPPSTRKDYPAAKRAKLDS

GRVLKQISNNRKCSSPRSSDTEENDKRRTHNVLERQRRNELKRSFFA

LRDQIPELENNEKAPKVVILKKATAYILSIQADEHKLTSEKDLLRKR

REQLKHKLEQLRNSGAGSGVKQTLNFDLLKLAGDVESNPGPMAVSDA

LLPSFSTFASGPAGREKTLRPAGAPTNRWREELSHMKRLPPLPGRPY

DLAATVATDLESGGAGAACSSNNPALLARRETEEFNDLLDLDFILSN

SLTHQESVAATVTTSASASSSSSPASSGPASAPSTCSFSYPIRAGGD

PGVAASNTGGGLLYSRESAPPPTAPFNLADINDVSPSGGFVAELLRP

ELDPVYIPPQQPQPPGGGLMGKFVLKASLTTPGSEYSSPSVISVSKG

SPDGSHPVVVAPYSGGPPRMCPKIKQEAVPSCTVSRSLEAHLSAGPQ

LSNGHRPNTHDFPLGRQLPTRTTPTLSPEELLNSRDCHPGLPLPPGF

HPHPGPNYPPFLPDQMQSQVPSLHYQELMPPGSCLPEEPKPKRGRRS

WPRKRTATHTCDYAGCGKTYTKSSHLKAHLRTHTGEKPYHCDWDGCG

WKFARSDELTRHYRKHTGHRPFQCQKCDRAFSRSDHLALHMKRHFGS

GEGRGSLLTCGDVEENPGPLEMAGHLASDFASSPPPGGGDGSAGLEP

GWVDSRTWLSFQGPPGGPGIGPGSEVLGISPCPPAYEFCGGMAYCGP

QVGLGLVPQVGVETLQPEGQAGARVESNSEGTSSEPCADRPNAVKLE

KVEPTPEESQDMKALQKELEQFAKLLKQKRITLGYTQADVGLTLGVL

FGKVFSQTTICRFEALQLSLKNMCKLRPLLEKWVEEADNNENLQEIC

KSETLVQARKRKRTSIENRVRWSLETMFLKCPKPSLQQITHIANQLG

LEKDVVRVWFCNRRQKGKRSSIEYSQREEYEATGTPFPGGAVSFPLP

PGPHFGTPGYGSPHFTTLYSVPFPEGEAFPSVPVTALGSPMHSNGSG

QCTNYALLKLAGDVESNNPGPMYNMMETELKPPGPQQASGGGGGGGN

ATAAATGGNQKNSPDRVKRPMNAFMVWSRGQRRKMAQENPKMHNSEI

SKRLGAEWKLLSETEKRPFIDEAKRLRALHMKEHPDYKYRPRRKTKT

LMKKDKYTLPGGLLAPGGNSMASGVGVGAGLGGGLNQRMDSYAHMNG

WSNGSYSMMQEQLGYPQHPGLNAHGAAQMQPMHRYVVSALQYNSMTS

SQTYMNGSPTYSMSYSQQGTPGMALGSMGSVVKSEASSSPPVVTSSS

HSRAPCQAGDLRDMISMYLPGAEVPEPAAPSRLHMAQHYQSGPVPGT

AKYGTLPLSHM (SEQ ID NO: 6)

Various combinations of exogenous reprogramming factors can be used to reprogram populations or subpopulations of NBCs. As described herein, the exogenous reprogramming factors are delivered to NBCs by introduction of one or more nucleic acid expression vectors (DNA expression vectors or RNA expression vectors) encoding the exogenous reprogramming factors. In some embodiments, the exogenous reprogramming factors to be expressed include the four factors Oct4, Sox2, Klf4, and c-Myc. In some embodiments the exogenous reprogramming factors include Oct4, Sox2, Klf4, c-Myc, and Nanog. In other embodiments, the exogenous reprogramming factors include (i) the four reprogramming factors Oct4, Sox2, Kl4, c-Myc, but without additional exogenous reprogramming factors, or (ii) the five reprogramming factors Oct4, Sox2, Klf4, c-Myc, and Nanog, but without additional exogenous reprogramming factors. In other embodiments, the four exogenous reprogramming factors include Oct4, Sox2, Nanog, and Lin-28, or Oct4, Sox2, Nanog, and Lin-28, but without additional exogenous reprogramming factors.

In further embodiments, the exogenous reprogramming factors include the three reprogramming factors Oct4, Sox2, and Klf4; or include Oct4, Sox2, and Kl4, but without additional exogenous reprogramming factors.

In some embodiments, the exogenous reprogramming factors do not include Tert or SV40 Large T-antigen.

In some cases, expression of each exogenous reprogramming factor is achieved by introducing a separate nucleic acid expression vector (e.g., a DNA expression vector) encoding the reprogramming factor into the NBCs to be reprogrammed. For example, in some cases four DNA expression vectors are introduced into a NBC host cell population or subpopulation to be reprogrammed, where each plasmid expression vector encodes and drives expression of a separate reprogramming factor in the host cells to be reprogrammed. In some embodiments, the four DNA expression vectors (e.g., plasmids or minicircles) separately encode Oct4, Sox2, Kl4, Sox2, and c-Myc. In other embodiments, the four DNA expression vectors encode Oct4, Sox2, Lin-28, and Nanog. In some cases, three separate DNA expression vectors encoding separately Oct4, Sox2, and Lin-28 are used in the reprogramming methods described herein.

In some cases, the reprogramming methods described utilize a combination of nucleic acid expression vectors, some of which encode and drive the expression of a single reprogramming factor (e.g., Oct4), and the others encoding two, three, or four reprogramming factors within a single, polycistronic expression cassette, as described herein. In some embodiments, two nucleic acid expression vectors are utilized, each encoding two reprogramming factors linked to each other by a 2A peptide or equivalent "autocleavage." In some embodiments, the two nucleic acid expression vectors encode Oct4 and Sox2, and c-Myc and Klf4. In some cases, the two nucleic acid expression vectors are DNA expression vectors. In other cases, the two nucleic acid expression vectors are RNA expression vectors.

In some cases, where DNA expression vectors encoding the reprogramming factors are under the control of an inducible promoter requiring an exogenous transactivator (e.g., the reverse tetracycline transactivator or "rtTA"), a nucleic acid expression vector for expression of the transactivator is introduced into the NBCs in addition to the one or more nucleic acids encoding the reprogramming factors. In some embodiments, the nucleic acid expression vector encoding the transactivator is introduced into the NBCs at same time as one or more nucleic acid expression vectors encoding reprogramming factors. In other embodiments, the nucleic acid expression vector encoding the transactivator is introduced into the NBCs at a different time than the nucleic acid expression vectors encoding the reprogramming factors. In one embodiment, the reprogramming methods described herein include introducing a DNA expression vector that includes a polycistronic expression cassette for expression of Oct4, Sox2, Klf4, and Sox2 under the control of an inducible Tet-O promoter and a separate DNA expression vector containing an expression cassette for rtTA under the control of a constitutive promoter suitable for expression in NBCs or NBC subpopulations.

In some embodiments, the nucleic acid expression vector encoding one or more reprogramming factors further encode within the same expression cassette one or more selection markers that facilitates identification or selection of NBCs that have received and express the reprogramming factors along with the selection marker. Examples of marker genes include, but are not limited to, genes encoding fluorescent proteins, e.g., Fluorescent Timer, tandem-dimer (td)-Tomato mCherry, EGFP, DS-Red, monomeric Orange, YFP, and CFP; genes encoding proteins conferring resistance to a selection agent, e.g., the, $Puro^R$, $Puro^R$-$\Delta TK$, $Zeo^R$, $Hygro^R$ $neo^R$ gene, and the blasticidin resistance gene. In some cases, the selection marker contains the amino acid sequences of a fluorescent reporter and a selection marker enzyme protein sequence fused to each other. Examples of such fusion selection markers include, but are not limited to, EGFP-$Puro^R$, EGFP-$Hygro^R$, Fluorescent Timer-$Puro^R$, and mCherry-$Hygro^R$.

With respect to the nucleic acid and amino acid sequences described herein, in some embodiments sequence variants (e.g., reprogramming factor sequence variants) may be utilized. In general, polypeptide sequence variants, include functional variants (as determined by appropriate assays) comprising an amino sequence at least 75%, e.g., at least 80%, 85%, 90%, 95%, or any other percent identical to those disclosed herein. With regard to the polypeptide sequences described herein and variants thereof, the structural and functional homology of two or polypeptides generally includes determining the percent identity of their amino acid sequences to each other. Sequence identity between two or more amino acid sequences is determined by conventional methods. See, for example, Altschul et al., (1997), *Nucleic Acids Research*, 25(17):3389-3402; and Henikoff and Henikoff (1982), *Proc. Natl. Acad. Sci. USA*, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences]) (100).

Those skilled in the art will appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman (1988), *Proc. Nat'l Acad. Sci. USA*, 85:2444, and by Pearson (1990), *Meth. Enzymol.*, 183:63. Briefly, FASTA first characterizes sequence similarity by identifying regions shared by the query sequence and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch (1970), *J. Mol. Biol.*, 48:444-453; Sellers (1974), *SIAM J. Appl. Math.*, 26:787), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson (1990), *Meth. Enzymol.*, 183:63.

Suitable nucleic acids that may be utilized for the methods described herein hybridize specifically under low, medium, or high stringency conditions to a probe of at least 1000 nucleotides from a nucleic acid encoding the amino acid sequence of any of SEQ ID NOs:2, 4, 6, human Oct4, Sox2, Klf4, c-Myc, Nanog, or Lin-28. Low stringency hybridization conditions include, e.g., hybridization with a 1000 nucleotide probe of about 40% to about 70% GC content; at 42° C. in 2×SSC and 0.1% SDS. Medium stringency hybridization conditions include, e.g., at 50° C. in 0.5×SSC and 0.1% SDS. High stringency hybridization conditions include, e.g., hybridization with the above-mentioned probe at 65° C. in 0.2×SSC and 0.1% SDS. Under these conditions, as the hybridization temperature is elevated, a nucleic acid with a higher homology can be obtained.

A number of considerations are useful to the skilled artisan in determining if a particular amino acid sequence variant of the polypeptides described herein is suitable for use in the methods described herein. These considerations include, but are not limited to: (1) known structure-function relationships such as a DNA binding domain or a transactivation domain; (2) the presence of amino acid sequence conservation among naturally occurring homologs (e.g., in paralogs and orthologs) of the polypeptide, as revealed by sequence alignment algorithms as described herein. Notably, a number of bioinformatic algorithms are known in the art that successfully predict the functional effect, i.e., "tolerance" of particular amino substitutions in the amino acid sequence of a protein on its function. Such algorithms include, e.g., pMUT, SIFT, PolyPhen, and SNPs3D. For a review see, e.g., Ng and Henikoff (2006), *Ann Rev Genomics Hum Genet.*, 7:61-80. For example, pMUT predicts with a high degree of accuracy (about 84% overall) whether a particular amino acid substitution at a given sequence position affects a protein's function based on sequence homology. See Ferrer-Costa et al., (2005), *Bioinformatics*, 21(14):3176-3178; Ferrer-Costa et al., (2004), *Proteins*, 57(4):811-819; and Ferrer-Costa et al., (2002), *J Mol Biol*, 315:771-786. The PMUT algorithm server is publicly available on the world wide web at: mmb2.pcb.ub.es:8080/PMut. Thus, for any polypeptide amino acid sequence, an "amino acid substitution matrix" can be generated that provides the predicted neutrality or deleteriousness of any given amino acid substitution on a given protein's function(s).

Non-naturally occurring sequence variants can be generated by a number of known methods. Such methods include, but are not limited to, "Gene Shuffling," as described in U.S. Pat. No. 6,521,453; "RNA mutagenesis," as described in Kopsidas et al., (2007), *BMC Biotechnology*, 7:18-29; and "error-prone PCR methods." Error prone PCR methods can be divided into (a) methods that reduce the fidelity of the polymerase by unbalancing nucleotides concentrations and/or adding of chemical compounds such as manganese chloride (see, e.g., Lin-Goerke et al., (1997), *Biotechniques*, 23:409-412), (b) methods that employ nucleotide analogs (see, e.g., U.S. Pat. No. 6,153,745), (c) methods that utilize 'mutagenic' polymerases (see, e.g., Cline, J. and Hogrefe, H. H. (2000), *Strategies* (Stratagene Newsletter), 13:157-161 and (d) combined methods (see, e.g., Xu et al., (1999), *Biotechniques*, 27:1102-1108. Other PCR-based mutagenesis methods include those, e.g., described by Osuna et al., (2004), *Nucleic Acids Res.*, 32(17):e136 and Wong et al., (2004), *Nucleic Acids Res.*, 10; 32(3):e26), and others known in the art.

Introduction of Nucleic Acid Expression Vectors into NBCs

In some embodiments of the reprogramming methods described herein, any of the above-described nucleic acid expression vector combinations are introduced into NBCs by transfection only within a single period no greater than about 40 hours, e.g., no greater than 36 hours, 34 hours, 33 hours, 30 hours, 28 hours, 26 hours, 24 hours, 22 hours, 18 hours, 16 hours, or another period no greater than about 40 hours. In some embodiments, transfection of the NBCs with the one or more DNA expression vectors encoding the reprogramming factors (e.g., Oct4, Sox2, Klf4, and c-Myc) are introduced by transfection into the NBCs only once. In some embodiments, where the one transfection is done by electroporation (e.g., by nucleoporation) or any other method in the art that rapidly introduces nucleic acids into cells (e.g., biolistics, or laser-pulse-mediated transfection), the electroporation may include multiple electroporation pulses within a period less than about 30 minutes, but this will be understood herein to be one transfection only.

Nucleic acid expression vectors, e.g., DNA expression vectors encoding reprogramming factors can be introduced into NBCs or NBC subpopulations by a variety of methods known in the art. Examples of high efficiency transfection efficiency methods include capillary electroporation, as described in Kim et al (2008), *Biosensors and Bioelectronics*, 23:1353-1360, and in PCT Patent Application Publication No. WO2009129327, which is commercially available under the trade name Neon™ (Invitrogen, Carlsbad, Calif.); "nucleofection," as described in, e.g., Trompeter (2003), *J Immunol. Methods*, 274(1-2):245-256, and in international patent application publications WO2002086134, WO200200871, and WO2002086129, transfection with lipid-based transfection reagents such as Fugene® 6 and Fugene® HD(Roche), DOTAP, and Lipofectamine™ LTX in combination with the PLUS (Invitrogen, Carlsbad, Calif.), Dreamfect™ (OZ Biosciences, Marseille, France), GeneJuice™ (Novagen, Madison, Wis.), polyethylenimine (see, e.g., Lungwitz et al., (2005), *Eur. J Pharm. Biopharm.*, 60(2):247-266), and Gene-Jammer™ (Stratagene, La Jolla, Calif.), and nanoparticle transfection reagents as described in, e.g., U.S. patent application Ser. No. 11/195,066. Methods for preparation of transfection-grade nucleic acid expression vectors and transfection methods are well established. See, e.g., Sambrook and Russell (2001), "Molecular Cloning: A Laboratory Manual," 3$^{rd}$ ed, (CSHL Press); and *Current Protocols in Molecular Biology*, John Wiley & Sons, N.Y. (2005), 9.1-9.14.

In some cases, in the transfection step for the reprogramming methods described herein, a suitable ratio of nucleic acid vector mass (in culture solution) to cells (e.g., NBCs) for each nucleic acid expression vector to be introduced ranges from about 0.1 mg/$10^5$ cells to about 3.0 mg/$10^5$ cells, e.g., 0.20 mg/$10^5$ cells, 0.5 mg/$10^5$ cells, 0.75 μg/$10^5$ cells, 1.0 mg/$10^5$ cells, 1.5 μg/$10^5$ cells, 1.75 mg/$10^5$ cells, 2.0 μg/$10^5$ cells, 2.3 mg/$10^5$ cells, 2.7 μg/$10^5$ cells, or another vector mass to cell ratio from about 0.1 mg/$10^5$ cells to about 3.0 mg/$10^5$ cells. In some embodiments, a suitable vector copy number to cell ratio ranges from about 70,000 copies (in culture solution)/cell to about $2\times10^6$ copies (in culture solution)/cell, e.g., 100,000 copies/cell, 200,000 copies/cell, 400,000 copies/cell, 650,000 copies/cell, 800,000 copies/cell, $1.0\times10^6$ copies/cell, $1.2\times10^6$ copies/cell, $1.5\times10^6$ copies/cell, $1.75\times10^6$ copies/cell, or another vector copy number to cell ratio from about 70,000 copies/cell to about $2.0\times10^6$ copies/cell.

Where, multiple nucleic acid vectors are to be introduced, their mass ratios, or their copy number ratios may be varied from about 1:10 to about 10:1, e.g., 1:8, 1:7, 1:4, 1:3, 1:1, 2:1, 3:1, 4:1, 6:1, 8:1, or another mass or copy number ratio from about 1:10 to about 10:1. For example, in some embodiments, where nucleic acid vectors encoding Oct4, Sox2, Klf4, and c-Myc are introduced into the NBCs to be reprogrammed, Oct 4 is introduced at a copy number stoichiometric ratio of 3:1 relative to the one or more expression cassettes encoding the other three reprogramming factors. In one embodiment, the reprogramming method comprises introducing one nucleic acid expression vector encoding Oct4, and another containing a polycistronic expression cassette encoding c-Myc-, Klf4, and Sox2. In some embodiments, the method includes the use of one DNA expression vector containing a polycistronic vector encoding, c-Myc, Klf4, Oct2, and Sox2 interconnected by an encoded 2A polypeptide, and under the control of a tet-inducible promoter, or another inducible promoter known in the art, and another nucleic acid expression vector encoding the cognate transactivator for the inducible promoter, e.g., rtTA for a tet-inducibled promoter, and allowing constitutive expression of the encoded transactivator, where the nucleic acid expression vectors are provided at a mass ratio of 1:2.

In some embodiments, the reprogramming methods include introducing into NBCs or subpopulations of NBCs by electroporation one or more DNA expression vectors encoding a combination of reprogramming factors including any of the following: (a) Oct4, Sox2, Klf4, and c-Myc; (b) Oct4, Sox2, and Klf4; (c) Oct4, Sox2, Klf4, c-Myc, and Nanog; or (d) Oct 4, Sox2, Lin-28, and Nanog.

In one exemplary embodiment, the electroporation method is a capillary electroporation method, as described in Kim et al (2008), *Biosens Bioelectron*, 23(9):1353-1360, U.S. Patent Application Publication No. 20070275454. In some embodiments, capillary electroporation is performed on about 50,000 cells to about $1\times10^6$ cells, e.g., 75,000 cells, 100,000 cells, 200,000 cells, 400,000 cells, 500,000 cells, 700,000 cells or another number of cells from about 50,000 cells to about $1\times10^6$ cells. Typically, the capillary electroporation is performed in a volume of about 5 μl to about 20 μl of a suitable transfection buffer containing the nucleic acid expression vectors to be introduced, e.g., 10 μl, 12 μl, 15 μl, or another volume of vector-containing transfection buffer from about 5 μl to about 20 μA Capillary electroporation parameters that may be optimized include, pulse voltage, pulse time, and number of pulses. Pulse voltage may range from about 1500V to 3500V, e.g., about 1600V, 1700V, 1800V, 1850V, 1900V, 1950V, 2000V, 2100V, 2200V, 2500V, 2700V, 3000V, 3200V, or another voltage from about 1500V to about 3500V. Pulse duration may range from about 10 milliseconds (ms) to about 40 ms, e.g., about 15 ms, 20 ms, 25 ms, 27 ms, 30 ms, 32 ms, 35 ms, or another pulse duration from about 10 ms to about 40 ms. The number of pulses may be 1, 2, or 3 pulses. In some embodiments, one or more nucleic acid expression vectors are introduced into NBCs by capillary electroporation with 1 pulse at 1900V for 30 ms.

Culture of Cells for hiPS Cell Line Derivation Following Transfection

After electroporation NBCs are transferred to 96-well ultra low attachment (ULA) plates in a volume of about 200 μl/well of a medium suitable for culture of NBCs or subpopulations of NBCs ("hematopoietic culture medium"). After about 24 hours, transfected NBCs are transferred to 24 well plates in a volume of the same medium of about 0.5 ml to about 1.5 ml, e.g., about 0.7 ml, 0.8 ml, 1.0 ml, 1.2 ml, 1.3 ml, or another volume of medium from about 0.5 ml to about 1.5 ml. In some embodiments, culture of the transfected NBCs is continued in hematopoietic culture medium within ULA tissue culture ware (e.g., 96-well plates) for about two to about six days, e.g., about three, four, five, or another culture period from about two to about six days in hematopoietic culture medium. In some embodiments, where expression of encoded reprogramming factors is under inducible control of a transactivator (e.g., rtTA), the inducing agent (e.g., doxycycline) is added after about one to about three days following transfection to induce expression of the reprogramming factors in the NBCs. Examples of suitable base media include, but are not limited to, HSC GEM (Stemgenix; Amherst, N.Y.)/Stemline (Sigma-Aldrich; St. Louis, Mo.) Hematopoietic Stem Cell Expansion Medium, X-VIVO™ 15 (BioWhittaker; Walkersville, Maryland), HPGM (BioWhittaker; Walkersville, Maryland), CellGro® SCGM (Cellgenix, Gaithersburg, Md.), QBSF-60 (Quality Biological, Gaithersburg, Md.), HemaPro™ (Celox, St. Paul, Minn.), StemPro®-34 (Life Technologies; Grand Island, N.Y.) and StemSpan H2000™/StemSpan SFEM (StemCell Technologies; Vancouver, British Columbia)StemPro®-34 medium (Invitrogen). In some embodiments, the foregoing media contain stem cell factor (SCF), thrombopoietin (TPO), and granulocyte macrophage colony stimulating factor (GM-CSF) at 100 ng/ml. In some embodiments, the suitable medium is Sigma Stemline® Dendritic Cell Maturation Medium (Sigma, Catalog #S3444) containing penicillin/streptomycin, β-mercaptoethanol, SCF at 100 ng/ml, granulocyte macrophage colony stimulating factor (GM-CSF) at 20 ng/ml (growth factors from R&D systems), and interleukin 4 (IL-4) at 20 ng/ml.

Following the period of hematopoietic culture, transfected NBCs are transferred to 24-well Matrigel™—(or other extracellular matrix substrate) coated cell culture plates, in a medium that is composed of about 50% medium suitable for hematopoietic cell lineages and 50% of a medium suitable for human embryonic stem (ES) or hiPS cell medium. Subsequently, a complete hiPS medium change is then carried out about every two to about four days. Suitable media for hiPS culture, particularly under feeder cell-free conditions, for the methods described herein include, but are not limited to, mTeSR™ (available, e.g., from StemCell Technologies, Vancouver, Canada), See, e.g., Ludwig et al, (2006), *Nat Biotechnol.*, 24(2):185-187. In other cases, alternative culture conditions for growth of hiPS cells are used, as described for human ES cells in, e.g., Skottman et al., (2006), *Reproduction*, 132 (5):691-698. Typically, culture medium suitable for maintenance and passaging of hiPS cells includes fibroblast growth factor (FGF-2) at a concentration of about 5 ng/ml to about 100 ng/ml. In some cases, hiPS cells may be cultured under xeno-free conditions, e.g., in "RegES" medium as described in Rajala et al (2010), *PLoS One*, 5(4):e10246. In some embodiments, the transfected NBCs are plated on mouse embryonic fibroblast (MEF) feeder cells in hES culture medium.

In some cases after about 20 days to about 40 days of maintaining transfected NBCs in hiPS cell medium (e.g., mTeSe), e.g., about 21 days, 22 days, 24 days, 26 days, 30 days, 32 days, 34 days, 36 days, or another period from about 20 days to about 40 days, cultures are monitored for the presence of adherent colonies of hiPSCs, which typically are made up of small cells having a high nucleus to cytoplasm ratio. Individual colonies are then picked and transferred individually to new wells for subcloning and characterization.

After obtaining and characterizing hiPS cells, a vector excision step, e.g., expression of a transposase or recombinase, is not necessary to remove DNA expression vectors that had been introduced during transfection of human NBCs In some embodiments, transfected NBCs are cultured in the presence of an inhibitor of the TGF-β receptor pathway to enhance the efficiency of reprogramming as described in International Patent Application No. PCT/US 10/26451. Examples of suitable TGF-β receptor pathway inhibitors include, but are not limited to, TGF-β receptor pathway inhibitors having the structure of any of Compounds I-IV:

Compound I

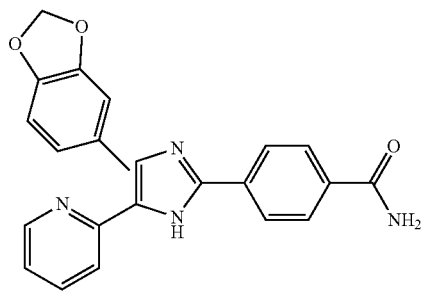

Compound II

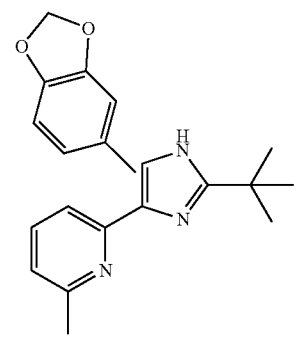

Compound III

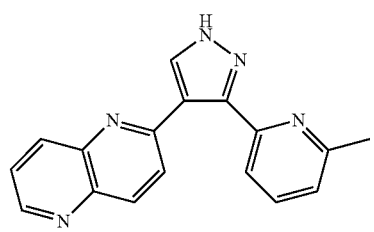

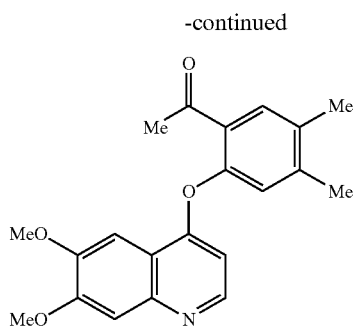

Compound IV

Suitable concentrations of the foregoing compounds range from about 1.0 µM to about 30 µM, e.g., about 2 µM, 5 µM, 10 µM, 12 µM, 15 µM, 20 µM, 25 µM, or another concentration from about 1.0 µM to about 30 µM. In some embodiments, transfected NBCs are cultured in the presence of the TGF-β receptor pathway inhibitor until putative hiPS cell colonies are identified. In other cases, the transfected NBCs are cultured in the presence of the TGF-β receptor pathway inhibitor for a more limited period of time following transfection, e.g., about 2 days to 30 days, e.g., about 3 days, 4 days, 5 days, 7 days, 10 days, 12 days, 14 days, 16 days, 21 days, 24 days, or another culture period from about 2 days to 30 days.

The production of integration-free hiPS cells by the reprogramming methods described herein does not require the expression of a recombinase or transposase in putative hiPS cells to excise one or more DNA expression vectors encoding reprogramming factors following identification and subcloning of putative hiPS cell colonies. Examples of recombinases and transposases include, but are not limited to, Cre-Recombinase, PiggyBac transposase, and Sleeping Beauty transposase. In some embodiments, the methods described herein do not include introducing or expressing a recombinase or transposase in hiPS cells following the identification of putative hiPS cell colonies as described herein. Typically, the methods described herein do not include an excision step to (e.g., by expression of a transposase or recombinase) remove DNA expression vectors from hiPS cells to generate integration-free hiPS cells.

The absence of integrated exogenous nucleic acids within hiPSCs derived the methods described herein may be determined by any of a number of standard methods known in the art, which include, but are not limited to genomic PCR and Southern blot hybridization to detect the presence of exogenous vector and/or exogenous transgene sequences within the genome of NBC-derived hiPSCs.

Analysis of hiPS Cells

Methods for identifying hiPS cells and hiPS cell colonies are known in the art. For example, putative iPS cell colonies may be tested for alkaline phosphatase (ALP) activity, and if positive, may then be assayed for expression of a series of human embryonic stem cell marker (ESCM) genes including, but not limited to, Nanog, E-Cadherin, DNMT3b, TDGF1, Lin-28, Dnmt3b, Zfp42, FoxD3, GDF3, CYP26A1, TERT, Oct 3/4, Sox2, Rex1, Sall4, and HPRT. See, e.g., Assou et al., (2007), *Stem Cells*, 25:961-973. Many methods for gene expression analysis are known in the art. See, e.g., Lorkowski et al., (2003), *Analysing Gene Expression, A Handbook of Methods: Possibilities and Pitfalls*, Wiley-VCH. Examples of suitable nucleic acid-based gene expression assays include, but are not limited to, quantitative RT-PCR (qRT-PCR), microarray hybridization, dot blotting, RNA blotting, RNAse protection, and SAGE.

In some embodiments, levels of ESCM gene mRNA expression levels in putative iPS cells colonies are determined by qRT-PCR. Putative iPS cell colonies are harvested, and total RNA is extracted using the "Recoverall total nucleic acid isolation kit for formaldehyde- or paraformaldehyde-fixed, paraffin-embedded (FFPE) tissues" (manufactured by Ambion, Austin, Tex.). In some instances, the colonies used for RNA extraction are fixed colonies, e.g., colonies that have been tested for ALP activity. The colonies can be used directly for RNA extraction, i.e., without prior fixation. In an exemplary embodiment, after synthesizing cDNA from the extracted RNA, the target gene is amplified using the TaqMan® PreAmp mastermix (manufactured by Applied Biosystems, Foster City, Calif.). Real-time quantitative PCR is performed using an ABI Prism 7900HT using the following PCR primer sets (from Applied Biosystems) for detecting mRNA of the above-mentioned ESCM genes: Nanog, Hs02387400_g1, Dnmt3b, Hs00171876_m1, FoxD3, Hs00255287_1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1). Putative hiPS cell colonies may be assayed by an immunocytochemistry method for expression of protein markers including, but not limited to, SSEA-3, SSEA-4, TRA-1-60, TRA-1-81, CD9, CD24, Thy-1, and Nanog. A wide range of immunocytochemistry assays, e.g., fluorescence immunocytochemistry assays, are known as described in, e.g., Harlow et al., (1988), *Antibodies: A Laboratory Manual* 353-355, Cold Spring Harbor Laboratory, Cold Spring Harbor, N.Y., and see also, *The Handbook—A Guide to Fluorescent Probes and Labeling Technologies* (2004), Molecular Probes, Inc., Eugene, Oreg. In some cases, immunofluorescence staining is followed by quantitation of the number of cells immunopositive for one or more of the above-mentioned ES-cell protein markers. Such quantitative methods include, but are not limited to flow cytometry and image cytometry.

It is generally believed that pluripotent stem cells have the ability to form a teratoma, comprising ectodermal, mesodermal, and endodermal tissues, when injected into an immunocompromised animal. Induced cells or induced pluripotent stem cells (iPS) or ES cell-like pluripotent stem cells may refer to cells having an in vitro long-term self-renewal ability and the pluripotency of differentiating into three germ layers, and said pluripotent stem cells may form a teratoma when transplanted into a test animal such as mouse.

The induced cells may be assessed for pluripotency in a teratoma formation assay in an immunocompromised animal model. The immunocompromised animal may be a rodent that is administered an immunosuppressive agent, e.g., cyclosporin or FK-506. For example, the immunocompromised animal model may be a SCID mouse. About $0.5 \times 10^6$ cells to about $2.0 \times 10^6$ cells e.g., $0.6 \times 10^6$ cells, $0.8 \times 10^6$ cells, $1.0 \times 10^6$ cells, $1.2.\text{times} \times 10^6$ cells, $1.5.\text{times} \times 10^6$ cells, $1.7 \times 10^6$ cells, or other number of induced cells from about $0.5 \times 10^6$ cells to about $2.0 \times 10^6$ cells induced cells/mouse may be injected into the medulla of a testis of a 7- to 8-week-old immunocompromised animal. After about 6 to about 8 weeks, the teratomas are excised after perfusing the animal with PBS followed by 10% buffered formalin. The excised teratomas are then subjected to immunohistological analysis. One method of distinguishing human teratoma tissue from host (e.g., rodent) tissue includes immunostaining for the human-specific nuclear marker HuNu. Immunohistological analysis includes determining the presence of ectodermal (e.g., neuroectodermal), mesodermal, and endodermal tissues. Protein markers for ectodermal tissue include, but are not limited to, nestin, GFAP, and integrin .beta.1. Protein markers for mesodermal tissue include, but are not limited to, collagen II, Brachyury, and osteocalcin. Protein markers for endodermal tissue include, but are not limited to, alpha-fetoprotein (alpha.-FP) and HNF3beta.

In some embodiments, the resulting integration free hiPSCs have a rearrangement in the immunoglobulin genomic locus (e.g., VJ, VDJ) or a rearrangement of the T-cell receptor genomic locus (e.g., VJ, VDJ). Such genomic rearrangements can be detected by a number of techniques known in the art, e.g., genomic PCR or Southern blot hybridization. In some embodiments, the resulting integration free hiPSCs comprise one or more genomic changes commonly associated with a B cell or T cell (e.g., junctional diversity, somatic recombination, somatic hypermutations, etc.).

EXAMPLES

Example 1

Generation of Integration-Free hiPS Cells by Transient Transfection of Nucleated Blood Cells with Reprogramming Factors Oct4, Sox2, Kl4, and c-Myc The original objective of this work was to evaluate the ability of the piggyBac plasmid/transposon reprogramming system (as described in Woltjen et al (2009), *Nature*, 458 (7239) 766-770) to reprogram PBMCs. This system, as reported in Woltejen et al (2009), utilizes piggyBac transposase to initially drive genomic integration of a transposon expression vector encoding four reprogramming factors (Klf4, c-Myc, Oct4, and Sox2) and a separate transposon vector encoding the reverse-tetracycline transactivator (rtTA) to drive expression in trans of the four reprogramming factors to induce reprogramming of somatic cells into iPS cells. Subsequently, the same transposase is transiently expressed to remove the integrated transposon(s) from the genome to obtain integration-free hiPS cells, although to date this system has only been demonstrated successfully in neonatal fibroblasts. The system described by Woltjen includes three components that are used for the reprogramming step:

(1) a transposon plasmid containing a Doxycycline-inducible ("tet-inducible") expression cassette encoding the open reading frames of Klf4, c-Myc, Oct4, and Sox2 linked to each other by the 2A peptide sequence followed by an IRES element and β-galactosidase (transposon reprogramming vector), which allows a polycistronic mRNA to be translated to yield the four separate reprogramming factors and the β-gal reporter protein; (2) a transposon plasmid containing an expression cassette for constitutive mammalian expression of the reverse-tetracycline transactivator (rtTA vector), which, in the presence of doxycycline drives expression of the four reprogramming factors from the above transposon expression vector; and (3) a constitutive mammalian expression plasmid for expression of the piggyBac transposase (PB vector). Thus, it was expected that transfection of these three plasmids in adult human NBCs followed by culture in the presence of doxycycline would yield hiPS cells with an integrated reprogramming vector. Surprisingly, it was found that while multiple hiPS cell lines were obtained following transfection of these plasmids and culture of human NBCs in the presence of doxycyline, none of the obtained hiPSC lines contained an integrated reprogramming vector Isolation of NBCs Whole blood was purchased from Zen-bio and shipped at either ambient or 4° C. overnight. Samples arrived on day 3 after blood draw. Typically 10 ml per donor were requested. Samples were then diluted 1:3 in Hanks buffered salt solution (HBSS) and layer over a 15 ml Ficoll-Hypaque gradient. Samples were spun at 445×g for 45 minutes with no brakes at room temperature. Mononuclear cell layer and granulocytes were then isolated. After washing the cells in HBSS remaining red blood cells were lysed using Tris Ammonium Chloride solution at 37° C. for 5 minutes. Remaining cells were washed two more times and counted.

In subsequent experiments cells were sorted after Ficoll density gradients using the MoFlo cell sorter and sorted based on the cell surface markers CD3, CD19, CD14 and CD15. Or such cells were isolated from whole blood using the Miltenyi whole blood MACS kit.

Delivery of Plasmid Vectors

Prior to electroporation, PBMCs (100,000 to 1,000,000) were pelleted at 445×g and resuspended in 10 µl of transfection buffer (Neon™ transfection system, Invitrogen) containing 0.5 µg PiggyBac transposase (PB) plasmid, 0.5 µg reverse tetracycline transactivator (rtTA) expression plasmid and 1 µg of plasmid containing a tet-responsive 2A peptide-linked 4 factor reprogramming cassette with KlF4, c-Myc, Oct4, and Sox2 flanked by piggyBac transposition elements (PB-MKOS plasmid). In one case, however, the PB plasmid was omitted. Electroporation was executed using the NEON system (Invitrogen) and conditions were 1900 V, 30 msec, single pulse Immediately after electroporation cells were transferred to 200 µl of dendritic cell media (Stemline, Sigma), containing Penicillin/Streptomycin, β-mercaptoethanol (55 µM), 100 ng/ml SCF, 20 ng/ml GM-CSF, 20 ng/ml IL-4 (all from R&D Systems) in 96-well Ultra-Low Attachment (ULA) plates (Corning).

Culture

After 24 hours, the cells were transferred to dendritic cell media, containing Penicillin/Streptomycin, β-mercaptoethanol (55 µM), 100 ng/ml SCF, 20 ng/ml GM-CSF, 20 ng/ml IL-4 and 2 µg/ml Doxycycline in 24-well ULA plates (Corning).

After 4-5 days post-transfection, cells were transferred to Matriger coated plates in the original media. Then 1 ml of mTESR™ medium was added. Subsequently, the medium was changed every 3-4 days by carefully removing the supernatant and replacing it with fresh mTESR™+2 µg/ml Doxycycline.

Clonal Isolation and Expansion

Characteristic colonies appeared around day 30 of culture and were isolated and expanded using standard technique.

Gene Expression Analysis hiPS cell total RNA was isolated using Qiagen RNeasy kit following manufacturer's instructions. RT-qPCR was performed using ABI reagents and Fluidigm Biomark instrument. Taqman probes used were Hs00170423_m1, Hs00171876_m1, HS00220998_m1, Hs00702808_s1, Hs02387400_g1, Hs00360675 m1, Hs00162669_m1, Hs00399279 m1, Hs99999905 m1, Hs99999902 m1, Hs01053049_s1. The Oct4 probe was custom designed. Data were analyzed using Fluidigm Gene Expression and Spotfire software.

Results

NBCs were isolated using a Ficoll-Hypaque density gradient and subsequently we introduced the following 3 plasmids into these cells using the NEON system: pBASE, a plasmid encoding the piggyBAC transposase; PB-rtTA, a plasmid encoding the reverse tetracycline transactivator flanked by the piggyBAC terminal repeats and PB-MKOS, a plasmid encoding the 4 transcription factors OCT4, KLF4, SOX2 and CMYC (all of which were mouse orthologs), as well as an IRES linked βgeo cassette conferring neomycin resistance and lacZ enzymatic activity, again flanked by the piggyBAC terminal repeats. In one experiment, as a negative control, the PB plasmid was omitted for the electroporation. After a single pulse delivery of these plasmids, the cells were allowed to recover at high density for 24 hours. Typically cell survival was around 50%. The next day we transferred all cells to a larger volume and added Doxycycline to induce the expression of the transgenes. After 4 days in hematopoietic media adaptation of the transfected NBCs to iPSC conditions was by transferring them onto Matrigel™ and added an equal volume of mTESR™ iPSC media. After an additional 3-4 days all media was carefully removed and the supernatant was harvested and centrifuged separately to recover loosely attached and floating cells. Floating cells were then resuspended in mTESR with Doxycycline and plated together with the adherent cells. This procedure was routinely performed twice a week until we saw the appearance of iPSC colonies at around day 30. Once colonies reached a suitable size we individually isolated them and plated them on a fresh plate of Matrigel in mTESR media. Out of 6 colonies from 3 different donors we were able to establish 6 iPSC lines (630.2, 630.6A, 630.6B, 71.67A, 71.67B, 71.89A) from 2 different donors in two independent experiments. Interestingly one of these lines (630.2 shown in FIG. 1) was derived from an experimental condition in which the PiggyBac transposase was not included in the transfection suggesting initially that either the other two plasmids integrated into the genome without the aid of a transposase or the plasmids remained episomal.

hiPS Cell Characterization

Figure 2:
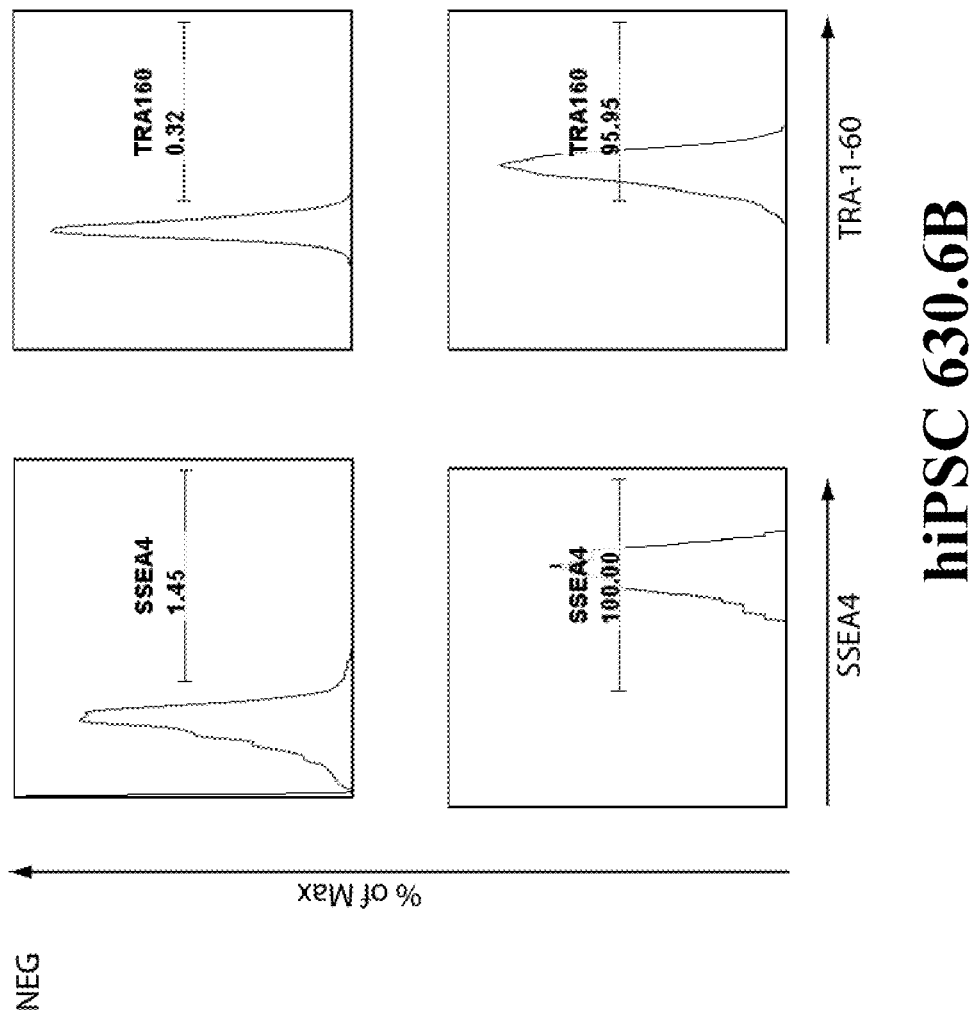
FIG. 2 shows quantitative flow sorting analysis for the pluripotent stem cell surface markers SSEA-4 and TRA 1-60 from the representative, integration-free hiPS cell line 630.6B (bottom panels). The top two panels show negative controls for staining of these cell surface markers. Staining for these two cell surface markers showed that 95% or greater of the analyzed 630.6B hiPSC line cells expressed SSEA-4 and TRA 1-60.
Figure 3:
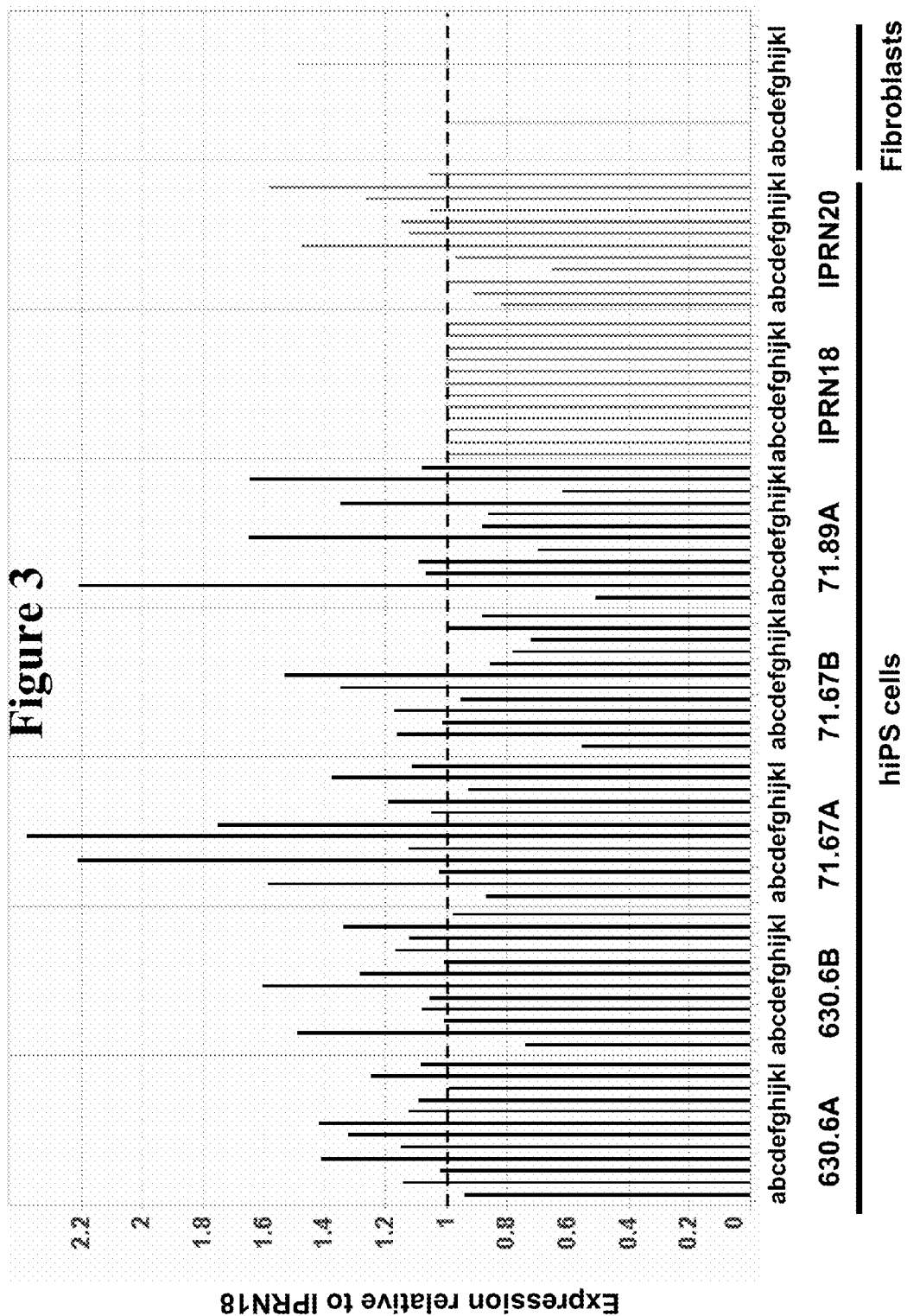
FIG. 3 is a bar graph depicting relative expression levels of a panel of pluripotency marker genes (a, E-CADHERIN; b, DNMT3b; d, GDF3; e, LIN28; f, NANOG; g, OCT4, I, SALL4; j, SOX2; k, TERT; 1, REX1) in the integration-free hiPS cell lines 630.6A, 630.6B, 71.67A, 71.67B, 71.89A compared to expression levels of these pluripotency gene markers in hiPS cell lines derived using retroviral delivery of transcription factors (IPRN18 and IPRN20), and adult human fibroblasts. None of the pluripotency marker genes are expressed in adult human Fibroblasts, but fibroblasts do express similar levels of housekeeping genes (c, GAPDH; h, RPLPO). Expression levels were normalized to the "housekeeping" gene GAPDH, and are shown as levels relative to iPSC line IPRN18. The expression values shown represent the mean value of duplicate reactions.

The iPSC lines were analyzed for the cell surface pluripotency marker expression of TRA-1-60 and SSEA4 by FACS analysis. Representative data are shown for hiPSC line 630.6B in FIG. 2. The six hiPSC lines were then characterized for expression of various pluripotency gene markers and compared to two hiPS cell lines (IPRN18 and IPRN20), previously established by retroviral transduction of the same four reprogramming factors, and fibroblasts. The results of this analysis are shown for five of these lines in FIG. 3, although the results were similar for hiPS line not shown in FIG. 3 (630.2). The panel of pluripotency markers included E-Cadherin ("a"), DNMT3b ("b"), GDF3 ("d"), Lin28 ("e"), Nanog ("f"), Oct4 ("g"), Sall4 ("i"), Sox2 ("j"), Tert ("k"), Rex1 ("l"); control "housekeeping genes" included GAPDH ("c") and RPLPO ("h"). The data were normalized to GAPDH expression and shown relative to expression level values for iPSC line IPRN18. The bars represent mean values of duplicate reactions. As shown, the expression pattern for the pluripotency markers within the five hiPS cell lines generated with plasmid vectors were quite similar to that observed in the two control hiPS cell lines, and strikingly different from the pluripotency marker expression pattern observed in fibroblasts. These data confirmed the status of these six lines as hiPS cell lines.

Figure 4:
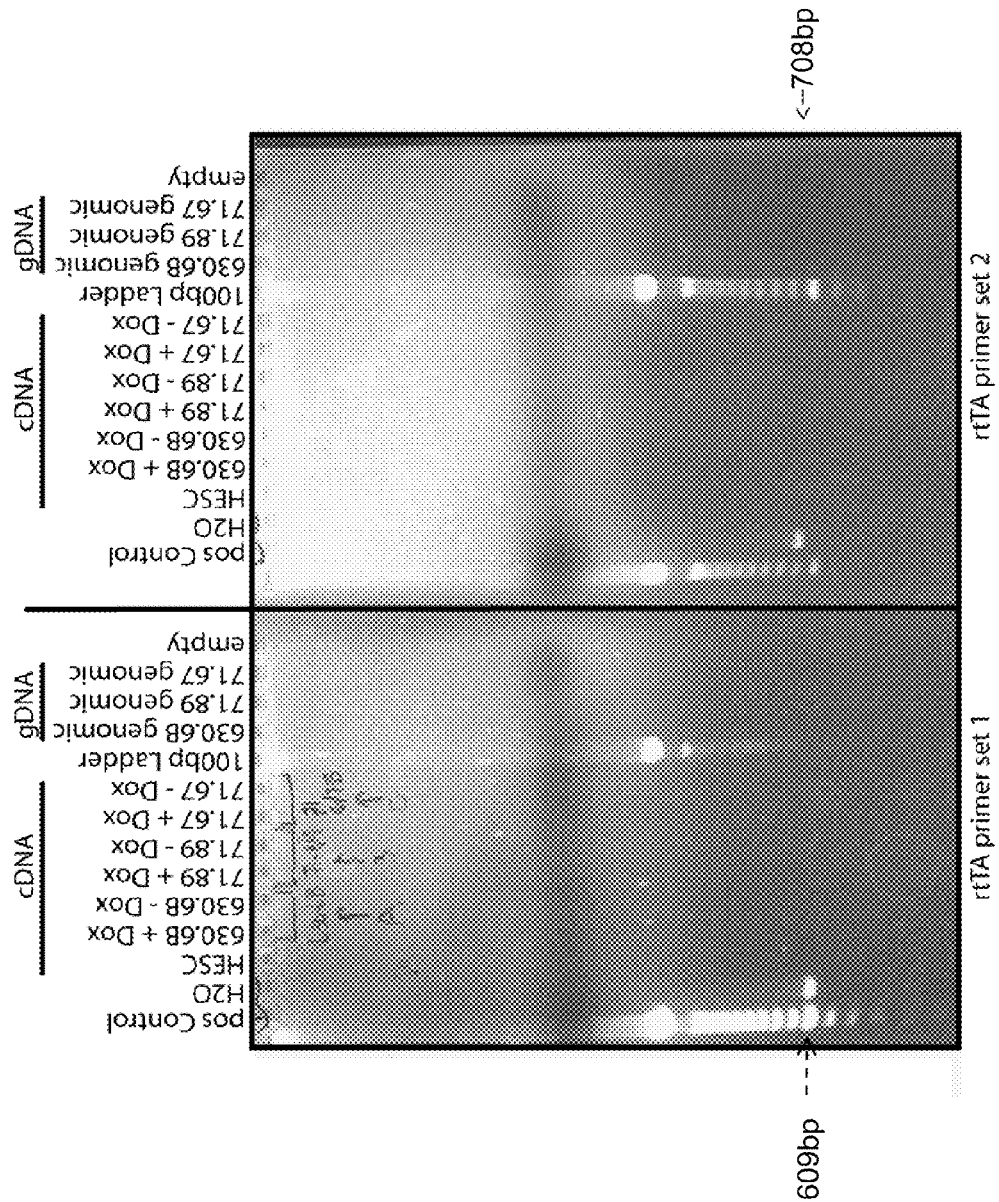
FIG. 4 shows agarose gel electrophoresis analysis of RT-PCR and genomic PCR for rtTA in hiPS cell lines 630.6B, 71.89, and 71.67 with separate primer pairs ("primer set 1" and "primer set 2," having one primer in common). The left panel shows PCR results using primer set 1. Lane 1 shows a 100 by ladder; lane 2 shows amplification from an rtTA plasmid positive control with the appropriate 609 by amplicon band; lane 3 is a water-only negative control PCR; lane 4 is from an hES (H7) cell line negative control PCR; lanes 5, 7, and 9 show RT-PCR results for rtTA in hiPS cell lines treated with Doxycyline (2 μg/ml); lanes 6, 8, and 10 show RT-PCR results for rtTA in the same hiPS cell lines, but in the absence of Doxycycline treatment (note that rtTA expression was under the control of a constitutive (CAG) promoter; lane 10 shows a 100 by ladder; lanes 11-13 show the results of genomic PCR for rtTA on the same hiPSC lanes. The right panel shows PCR results using primer set 2. The right panel shows the same configuration of lanes as the left panel, but results are from PCR reactions with a different primer pair (primer set 2). All of the hiPS cell lines tested negative for expression and genomic integration of the rtTA transgene indicating that the rtTA vector had been lost over the course of reprogramming nucleated blood cells.
Figure 5:
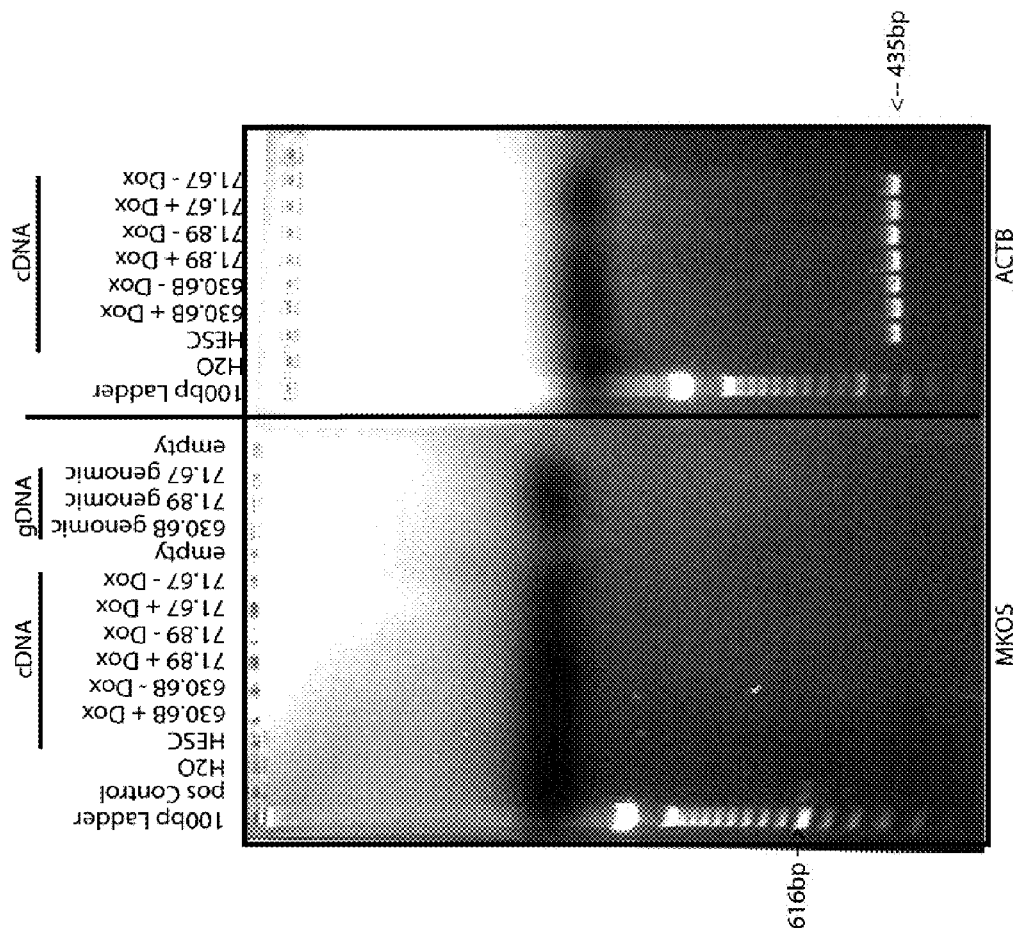
FIG. 5 shows agarose gel electrophoresis analysis of RT-PCR and genomic PCR for the Myc-Klf4-Oct4-Sox2 four reprogramming factor transgene and the endogenous actin gene in hiPS cell lines 630.6B, 71.89, and 71.67. The left panel shows PCR results using primer set 1. Lane 1 shows a 100 by ladder; lane 2 shows amplification from the PB-MKOS plasmid positive control with the appropriate 616 by amplicon band; lane 3 is a water-only negative control PCR; lane 4 is from an hES (H7) cell line negative control PCR; lanes 5, 7, and 9 show RT-PCR results for the expression of the MKOS transgene in hiPS cell lines treated with Doxycyline (2 μg/ml); lanes 6, 8, and 10 show RT-PCR results for rtTA in the same hiPS cell lines, but in the absence of Doxycycline treatment; lanes 11 is empty; lanes 12-14 show the results of genomic PCR for the MKOS transgene on the same hiPSC lanes. The right panel shows the results of RT-PCR analysis for expression of actin in the three hiPSC lanes as a positive control for the quality of the RNA samples and RT-PCR conditions. Lane 1 shows a 100 by ladder; lane 2 is a water-only negative control PCR; lane 3 is from an hES (H7) cell line positive control RT-PCR; lanes 4, 6, and 8 show RT-PCR results for the expression of the endogenous actin gene in hiPS cell lines treated with Doxycyline (2 μg/ml); lanes 5, 7, and 9 show RT-PCR results for actin in the same hiPS cell lines, but in the absence of Doxycycline treatment. All of the hiPS cell lines tested negative for expression of the MKOS transgene. Genomic PCR for the MKOS transgene (data not shown) likewise was negative for the presence of the MKOS transgene indicating that the PB-MKOS vector had been lost over the course of reprogramming nucleated blood cells.

No Exogenous Sequences are Expressed or Detected in the NBC-Derived hiPS Cell Lines Generated by Transfection Since the tet-inducible expression cassette of the PB-MKOS vector also encoded β-galactosidase, it was possible, in principle, to use tet-inducible β-galactosidase expression as a convenient marker for the presence/absence of the PB-MKOS and rtTA transposon vectors in the hiPS cell lines before and after genomic excision of these transposon vectors by transient expression of PB transposase. Surprisingly, no β galactosidase activity could be detected following treatment of the hiPS cell lines with Doxycycline (data not shown). This result suggested that at least one of the transposon vectors had been lost in all of these clonal lines, i.e., either the plasmid encoding the rtTA, the plasmid encoding the MKOS reprogramming cassette, or both. To confirm this we looked for: (A) the expression of the rtTA by RT-PCR, and genomic integration of the rtTA transgene by genomic PCR with two separate primer pairs in each experiment, and (B) the expression of the MKOS transgene by RT-PCR, and genomic integration of the MKOS transgene by genomic PCR with two separate primer pairs in each experiment. As shown for the three lines (630.6B, 71.89 and 71.67) in FIG. 4, we could not detect the rtTA either by RT-PCR (labeled "cDNA" in each panel) or PCR on genomic DNA (labeled "gDNA" in each panel), although a control plasmid did amplify (lane 2 in left and right panels). Similarly, as shown in FIG. 5 for the same three lines, we did not detect the expression of the MKOS plasmid by RT-PCR (labeled "cDNA" in left panel) or genomic PCR (labeled "gPCR" in left panel). On the other hand, abundant expression of the housekeeping gene ACTB was observed (right panel). We confirmed all of these results for the other three lines (data not shown), and also confirmed in all six lines that an actin amplicon could be detected by gPCR (data not shown). Based on these data, it was concluded that none of the transposon vectors had integrated into NBCs or the hiPS cell lines derived from the starting NBCs.

A preliminary genomic PCR analysis for rearrangement for the T-cell and B-cell receptor loci (data not shown) indicated that at least two of the clones, 630.6B and 71.67B, were derived from cells that had undergone T-cell receptor rearrangement, suggesting that at least two of the hiPS cell lines were of T-cell origin.

Based on these data, it was concluded that transient expression of the reprogramming factors in the transfected NBCs from the reprogramming plasmid vector during the reprogramming period was sufficient to induce hiPSCs without requiring genomic integration of any of the transfected plasmids. It is likely that a low level/absence of NBC proliferation in culture allows for persistent extrachromosomal expression of reprogramming factors at a high level and for a period sufficient to drive reprogramming Conversely, it may be that cell proliferation is necessary for transposon integration into the genome. While in the present experiments, a two plasmid, inducible vector system was used, it is believed that a one vector constitutive expression plasmid for expression of the four reprogramming factors would work equally well if not better. In summary, it is concluded that hiPSCs free of transgene/vector integration can be readily generated by transient transfection of one or more nucleic acid expression vectors for expression of reprogramming factors.

While preferred embodiments of the present invention have been shown and described herein, such embodiments are provided by way of example only. Numerous variations, changes, and substitutions are possible without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for generating integration-free human induced pluripotent stem cells, comprising transfecting human nucleated blood cells with one or more plasmid DNA expression vectors encoding reprogramming factors (a) Oct4, Sox2, Klf4, and c-Myc; (b) Oct4, Sox2, and Klf4; (c) Oct4, Sox2, Klf4, c-Myc, and Nanog; or (d) Oct 4, Sox2, Lin-28, and Nanog, expressing the encoded reprogramming factors in the transfected nucleated blood cells, and culturing the transfected nucleated blood cells under conditions adapted to growth of human induced pluripotent stem cells, identifying human induced pluripotent stem cell colonies, identifying integration-free human induced pluripotent stem cells that do not comprise exogenous DNA from the one or more plasmid DNA expression vectors, wherein:
  (i) at least two of the encoded reprogramming factors are linked by an intervening self-cleaving peptide sequence;
  (ii) the transfected human nucleated blood cells do not express an exogenous trans-acting factor that binds to a replication origin of an extra-chromosomal template or the one or more plasmid DNA expression vectors do not comprise a mammalian origin of replication sequence; and
  (iii) the transfection is performed only one time, or is performed only within a single 24 hour period.

2. The method of claim 1, wherein the one or more plasmid DNA expression vectors encode the reprogramming factors Oct4, Sox2, Klf4, and c-Myc.

3. The method of claim 1, wherein the one or more plasmid DNA expression vectors encode the reprogramming factors Oct4, Sox2, Klf4, c-Myc, and Nanog.

4. The method of claim 1, wherein the transfection comprises transfecting the nucleated blood cells with only one transfection method.

5. The method of claim 1, wherein the one or more plasmid DNA expression vectors further encode a reporter protein that is expressed in the transfected nucleated blood cells.

* * * * *